US006353153B1

(12) United States Patent
Ko et al.

(10) Patent No.: US 6,353,153 B1
(45) Date of Patent: *Mar. 5, 2002

(54) ENHANCED TRANSPORT WITH A PLASTID MEMBRANE TRANSPORT PROTEIN

(75) Inventors: Kenton Ko, Kingston; Peng Pang, Montreal, both of (CA)

(73) Assignee: Queen's University at Kingston, Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/300,681

(22) Filed: Apr. 27, 1999

Related U.S. Application Data

(63) Continuation-in-part of application No. PCT/CA97/00799, filed on Nov. 4, 1997, which is a continuation-in-part of application No. 08/747,788, filed on Nov. 14, 1996, now Pat. No. 5,919,999.

(51) Int. Cl.$^7$ .................. C12N 15/70; C12N 15/74; C12N 15/82

(52) U.S. Cl. ................ 800/278; 435/468; 435/471

(58) Field of Search .............. 435/69.1, 419, 435/411, 468, 252.3, 252.33, 252.31, 471; 536/23.4, 23.6; 800/278, 298, 306, 317.4

(56) References Cited

U.S. PATENT DOCUMENTS 5,919,999 A 7/1999 Ko et al. ............... 800/298

FOREIGN PATENT DOCUMENTS

| EP | 189707 | 8/1993 |
| EP | 0 735 140 A2 | 3/1996 |
| JP | 07 107 981 A | 4/1995 |
| WO | 94/08012 | 4/1994 |
| WO | 94/19471 | 9/1994 |
| WO | 95/25114 | 9/1995 |
| WO | 97/20941 | 6/1997 |

OTHER PUBLICATIONS

Akita, M., Sasaki, S., Matsuyama, S.–I., and Mizushima, S., "SecA interacts with secretory proteins by recognizing the positive charge at the amino terminus of the signal peptide in *Escherichia coli*", *J. Biol. Chem.* 265:8164–8169 (1990).
Alefsen, H., Waegemann, K., and Soll, J., "Analysis of the chloroplast protein import machinery", *J. Plant Physiol.* 144:339–345 (1994).
Aoyagi, N., Kuhlemeier, C., and Chua, N.–H., "The pea rbcS–3A enhancer–like element directs cell–specific expression in transgenic tobacco", *Mol. Gen. Genet.* 213:179–185 (1988).
Berghöfer, J., et al., "Isolation and Characterization of a cDNA Encoding the SecA Protein from Spinach Chloroplasts", *J. Biol. Chem.* 270(31):18341–18346 (1995).

De Block, M., "The cell biology of plant transformation: Current state, problems, prospects and the implications for the plant breeding", *Euphytica* 71:1–14 (1993).
Chrispeels, M.J., and Raikhel, N.V., "Short peptide domains target proteins to plant vacuoles", *Cell* 68:613–616 (1992).
Cline, K., Henry, R., Li, C., and Yuan, J., "Multiple pathways for protein transport into or across the thylakoid membrane", *EMBO J.* 12:4105–4114 (1993).
Cornwell, K.L, and Keegstra, K., "Evidence that a chloroplast surface protein is associated with a specific binding site for the precursor to the small subunit of ribulose–1, 5–bisphosphate carboxylase", *Plant Physiol.* 85:780–785 (1987).
Denèfle, P., Kovarik, S., Ciora, T., Gosselet, N., Bénichou, J.–C., Latta, M., Guinet, F., Ryter, A., and Mayaux, J.–F., "Heterologous protein export in *Escherichia coli*: influence of bacterial signal peptides on the export of human interleukin 1β", *Gene* 85:499–510 (1989).
Halpin, C., Elderfield, P.D., James, H.E., Zimmerman, R., Dunbar, B., and Robinson, C., "The reaction specificities of the thylakoidal processing peptidase and *Escherichia coli* leader peptidase are identical", *EMBO J.* 8:3917–3921 (1989).
Hinz, G., and Flügge, U.I., "Phosphorylation of a 51–kDa envelope membrane polypeptide involved in protein translocation into chloroplasts", *Eur. J. Biochem.* 175:649–659 (1988),
Hirsch, S., Muckel, E., Heemeyer, F., von Heijne, G., and Soll, J., "A receptor component of the chloroplast protein translocation machinery", *Science* 266:1989–1992 (1994).
Hockney, R.C., "Recent developments in heterologous protein production in *Escherichia coli*", *TiBtech* 12:456–463 (1994).
Holsters, M., de Waele, D., Depicker, A., Messens, E., van Montagu, M., and Schell, J., "Transfection and transformation of *Agrobacterium tumefaciens*", *Mol. Gen. Genet.* 163: 181–187 (1978).
Horsch, R.B., Fry, J.E., Hoffman, N.L., Eichholtz, D., Rogers, S.G., and Fraley, R.T., "A simple and general method for transferring genes into plants", *Science* 227:1229–1231 (1985).
Horsch, R.B., Fry, J., Hoffmann, N., Neidermeyer, J., Rogers, S.G., and Fraley, R.T.,"Leaf disc transformation", In *Plant Molecular Biology Manual* (eds. Gelvin et al.), Kluwer Acad. Publishers Dordrect, A5:1–9 (1988).
Kaderbhai, M.A., Pickering, T., Austen, B.M., and Kaderbhai, N., "A photoactivatable synthetic transit peptide labels 30 kDa and 52 kDa polypeptides of the chloroplast inner envelope membrane", *FEBS Lett.* 232:313–316 (1988).

(List continued on next page.)

Primary Examiner—Amy J. Nelson

(57) ABSTRACT

A novel method to enhance translocation of molecules across or into cellular membranes using a plastid protein transport gene is described. The method can also be used to incorporate substances into membranes of organisms. Nucleic acid constructs include those which express a plastid protein transport protein or its equivalent in cells of all organisms.

10 Claims, 8 Drawing Sheets-

OTHER PUBLICATIONS

Keegstra, K., Olsen, L.J., and Theg, S.M., "Chloroplastic precursors and their transport across the envelope membranes", *Annu. Rev. Plant Physiol. Plant Mol. Biol.* 40:471–501 (1989).

Kessler, F., Blobel, G., Patel, H.A., and Schnell, D.J., "Identification of two GTP–binding proteins in the chloroplast protein import machinery", *Science* 266:1035–1039 (1994).

Klee, H.J., Yanofsky, M.F., and Nester, E.W., "Vectors for transformation of higher plants", *Bio/Tech.* 3:637–642 (1985).

Klein, B.K., Polazzi, J.O., Devine, C.S., Rangwala, S.H., and Olins, P.O., "Effects of signal peptide changes on the secretion of bovine somatotropin (bST) from *Escherichia coli*", *Protein Eng.* 5:511–517 (1992).

Knott, T.G., and Robinson, C., "The SecA inhibitor, azide, reversibly blocks the translocation of a subset of proteins across the chloroplast thylakoid membrane", *J. Biol. Chem.* 269:7843–7846 (1994).

Ko, K., Bornemisza, O., Kourtz, L., Ko, Z.W., Plaxton, W.C., and Cashmore, A.R., "Isolation and characterization of a cDNA clone encoding a cognate 70–kDa heat shock protein of the chloroplast envelope", *J. Biol. Chem.* 267:2986–2993 (1992).

Ko, K., and Cashmore, A.R., "Targeting of proteins to the thylakoid lumen by the bipartite transit peptide of the 33 kd oxygen–evolving protein", *EMBO J.* 8:3187–3194 (1989).

Ko, K., Doung, C., and Ko, Z.W., "Nucleotide sequence of a *Brassica napus* C1p homolog", *Plant Physiol.* 104:1087–1089 (1994).

Ko, K. et al., "Isolation and characterization of a cDNA clone encoding a member of the Com44/Cim44 envelope components of the chloroplast protein import apparatus", *J. Biol. Chem.* 270:28601–28608 (1995).

Li, X., Henry R., Yuan, J., Cline, K., and Hoffman, N.E., "A chloroplast homologue of the signal recognition particle subunit SRP54 is involved in the posttranslational integration of a protein into thylakoid membranes", *Proc. Natl. Acad. Sci. USA* 92:3789–3793 (1995).

Ma, Y., Kouranov, A., LaSala, S.E., and Schnell, D.J., "Two components of the chloroplast protein import apparatus, IAP86 and IAP75, interact with the transit sequence during the recognition and translocation of precursor proteins at the outer envelope", *J. Cell Biol.* 134:315–327 (1996).

Morioka–Fujimoto, K., Marumoto, R., and Fukuda, T., "Modified enterotoxin signal sequences increase secretion level of the recombinant human epidermal growth factor in *Escherichia coli*", *J. Biol. Chem.* 266:1728–1732 (1991).

Nakai, M., Goto, A., Nohara, T., Sugita, D., and Endo, T., "Identification of the SecA protein homolog in pea chloroplasts and its possible involvement in thylakoidal protein transport", *J. Biol. Chem.* 269:31338–31341 (1994).

Nohara, T., Nakai, M., Goto, A., and Endo, T., "Isolation and characterization of the cDNA for pea chloroplast SecA. Evolutionary conservation of the bacterial–type SecA–dependent protein transport within chloroplasts", *FEBS Lett.* 364:305–308 (1995).

Odell, J.T., Nagy, F., and Chun, N.–H., "Identification of DNA sequences required for activity of the cauliflower mosaic virus 35S promoter", *Nature* 313:810–812 (1985).

Oliver, D.B., and Beckwith, J., "*E. coli* mutant pleitropically defective in the export of secreted proteins", *Cell* 25:765–772 (1981).

Oliver, D.B., Cabelli, R.J., Dolan, K.M., and Jarosik, G.P., "Azide–resistant mutants of *Escherichia coli* alter the SecA protein, an azide–sensitive component of the protein export machinery", *Proc. Natl., Acad. Sci. USA* 87:8227–8231 (1990).

Oliver, D.B., Cabelli, R.J., and Jarosik, G.P., "SecA protein: autoregulated initiator of secretory precursor protein translocation across the *E. coli* plasma membrane", *J. Bioenerg. Biomemb.* 22;311–336 (1990).

Oliver, D.B., "SecA protein: autoregulated ATPase catalysing preprotein insertion and translocation across the *Escherichia coli* inner membrane", *Mol. Microbiol.* 7:159–165 (1993).

Pain, D., Kanwar, Y.S, and Blobel, G., "Identification of a receptor for protein import into chloroplasts and its localization to envelope contact zones", *Nature* 331:232–237 (1988).

Pang, P., "A Component of the Chloroplast Protein Import Apparatus Functions in Bacteria." Unpublished master's thesis, Queen's University, Kingston, Ontario, Canada (1996).

Pérez–Pérez, J., Márquez, G., Barbero, J.–L., and Gutiérrez, J., "Increasing the efficiency of protein export in *Escherichia coli*", *Bio/Tech.* 12:178–180 (1994).

Perry, S.E., and Keegstra, K., "Envelope membrane proteins that interact with chlorplastic precursor proteins", *Plant Cell* 6:93–105 (1994).

Schnell, D.J., and Blobel, G., "Identification of intermediates in the pathway of protein import into chloroplasts and their localization to envelope contact sites", *J. Cell Biol.* 120:103–115 (1993).

Schnell, D.J., Blobel, G., and Pain, D., "The chloroplast import receptor is an integral membrane protein of chloroplast envelope contact sites", *J. Cell Biol.* 111:1825–1838 (1990).

Schnell, D.J., Kessler, F., and Blobel, G., "Isolation of components of the chloroplast protein import machinery", *Science* 266:1007–1012 (1994).

Seedorf, M., and Soll, J., "Copper chloride, an inhibitor of protein import into chloroplasts", *FEBS Lett.* 367:19–22 (1995).

Seedorf, M., Waegemann, K., and Soll, J., "A constituent of the chloroplast import complex represents a new type of GTP–binding protein", *Plant J.* 7:401–411 (1995).

Seidler, A., and Michel, H., "Expression in *Escherichia coli* of the psbO gene encoding the 33 kd protein of the oxygen–evolving complex from spinach", *EMBO J.* 9:1743–1748 (1990).

Simmons, L.C., and Yansura, D.G., "Translational level is a critical factor for the secretion of heterologous proteins in *Escherichia coli*", *Nature Biotech.* 14:629–634 (1996).

Soll, J., and Waegemann, K., "A functionally active protein import complex from chloroplasts", *Plant J.* 2:253–256 (1992).

Theg, S.M., and Scott, S.V., "Protein import into chloroplasts", *Trends Cell Biol.* 3:186–190 (1993).

van Dijl, J.M., de Jong, A., Smith, H., Bron, S., and Venema, G., "Signal peptidase I overproduction results in increased efficiencies of export and maturation of hybrid secretory proteins in *Escherichia coli*", *Mol. Gen. Genet.* 227:40–48 (1991).

Waegemann, K., Paulsen, H., and Soll, J., "Translocation of proteins into isolated chloroplasts requires cytosolic factors to obtain import competence", *FEBS Lett.* 261:89–92 (1990).

Waegemann, K., and Soll, J., "Characterization of the protein import apparatus in isolated outer envelopes of chloroplasts", *Plant J.* 1:149–158 (1991).

Woo, J.K., et al., "Chloroplast targeting of bacterial beta–glucuronidase with a pea transit peptide in transgenic tobacco plants", *Mol. Cells* 1:451–457 (1991).

Wu, C., and Ko, K., "Identification of an uncleavable targeting signal in the 70–kilodalton spinach chloroplast outer envelope membrane protein", *J. Biol. Chem.* 268:19384–19391 (1993).

Wu, C., Seibert, F.S., and Ko, K., "Identification of chloroplast envelope proteins in close physical proximity to a partially translocated chimeric precursor protein", *J. Biol. Chem.* 269:32264–32271 (1994).

Yuan, J., Henry, R., McCaffery, M., and Cline, K., "SecA homolog in protein transport within chloroplasts: evidence for endosymbiont–derived sorting", *Science* 266:796–798 (1994).

Gray, J.C. and Row, P.E., "Protein translocation across chloroplast envelope membranes," *Trends Cell Biol.* 5:243–7 (1995).

Pang, P. et al., "A component of the chloroplast protein import apparatus functions in bacteria," *J. Biol. Chem.* 272:(41):25623–25627 (1997).

Ko, K. et al., Oct. 29, 1997, GenBank Acc. No. X79091.

Ko, K. et al., May 6, 1994, EMBL Acc. N. X79091.

Nucleic Acid Sequence Encoding Bce44B

| | |
|---|---|
| CGTTGCTGTCGGCCACCACCACCATCTTCGTCAACCATAGGATCACACTTTTCTGGATTG | 60 |
| GTGTTGGGGTTGGGCTATCAGCTTTGTTCTCATGGGTAACCTCAAACGCAAAGAAATATG | 120 |
| CAATGCAAACAGCTATGAAGACAATGATGAACCAGATGAATACGCAAAACAGCCAGTTTA | 180 |
| ATAATCCTGGATTCCCAACAGGGGCAGGAGCAGGAGCAGGATCACCTTTTCCGTTTCCAT | 240 |
| TTCCTCCTCAAACAAGTCCTACTACCTCTCCGTTCCAGCCTCAATCCCAGTCTTCAGGTG | 300 |
| CTACTGTTGATCTGACAGCTACAAAAGTAGATAGGCCTCCTGTGTCTAAGCCACAACCTA | 360 |
| CACCTATACCTCCTACAAAGAGCATAGAAGTGTATAAACCAAGTGTTGTCGTAGAGGAAA | 420 |
| ACAAAGCGATGAAAGAAGAAAAGAACTACGCTTTTGAAGACGTTTCCCCTGAGGAAACCA | 480 |
| CAAAGGAAAGTCCATTTAGCAACTATGAAGAAGTCTCTGAAACTAGTGCCCCCAAAGAAA | 540 |
| CTCGCTTATTTGACGATGTTCTGCAAAATGGAGCTGCTCCGGCCAATGGTGCCACTGCTT | 600 |
| CAGATGTTTTTCAATCTTTGGGCGCTGGGAAGGATGGGCTGGTGGGTCAGTAGAAGTTT | 660 |
| TAGAGAAAATGATAGAATATCCCACATTTCAGAAGATGCTTTACCCACATTTGCCTGAGG | 720 |
| AGATGAGGAACCCAGAAAGTTTCAAATGGGTGCGTAAGAATCCTCAATACCGTCAACAGC | 780 |
| TACAGGACATGTTGAATAATATGAGTGAGAGTGGTGAATGGACAAGAGAATGACGGAGA | 840 |
| CCTTAAAGAATTTTGACCCGAATAGCCCCGAAGTTAAGCAAGGATTCGATCAATTAGGAC | 900 |
| TGACTCCAGAAGAAGTCATCTCTAAGATAATGGAGAACCCTGATGTTTCAATGGCATTCC | 960 |
| AGAATCCTAGAGTCGAAGCAGCGTTAATGGACTGCTCAGAGAACCCGATGAACATCATGA | 1020 |
| AGTACCAAAATGACAAGAGGTAATGGATGTGTTCAACAAGATATCGCAGCTCTTCCCAG | 1080 |
| GATTGACGGGTTGAAAAGGCTCGCTGATCACGTCTTTTGGTTTAATGACTTTTATCTTAT | 1140 |
| TGGATCAGAGGTTCATGTCTTTCTTTAGCTTTGTACCACTGAGAAAAAAAAAA | 1193 |

FIGURE 1

Amino Acid Sequence of Bce44B protein

```
MQTAMKTMMNQMNTQNSQFNNPGFPTGAGAGAGSPFPFPFPPQTSPTTSPFQPQSQSSGA    61
TVDLTATKVDRPPVSKPQPTPIPPTKSIEVYKPSVVVEENKAMKEEKNYAFEDVSPEETT   121
KESPFSNYEEVSETSAPKETRLFDDVLQNGAAPANGATASDVFQSLGAGKGWAGGSVEVL   181
EKMIEYPTFQKMLYPHLPEEMRNPESFKWVRKNPQYRQQLQDMLNNMSESGEWDKRMTET   241
LKNFDPNSPEVKQGFDQLGLTPEEVISKIMENPDVSMAFQNPRVEAALMDCSENPMNIMK   301
YQNLKEVMDVFNKISQLFPGLTG
```

FIGURE 2

```
GATTTGGTTCAAATACATCTGACAGTACCTCATCAACGGGAAAATCTAATCCTCTATTGT
CGGTGGATGCTCTGGAGAAAATGATGGAAGATCCAACAGTGCAGAAGATGGTTTACCCT
ATCTACCCGAGGAGAGATGAGGAACATTAAAATGATGCTACAAAATCCACAAT
ACCGTCAACATGGAGGACATGATGAATAACATGGGTGGAAACCCAGAATGGGACAACC
GCATGATGGATTCCTGAAGAATTTTGATCTCAGCAGCCCTGAAATCAAGCAACAATTG
ATCAGATAGGACTTACTCCCGAGGAAGTCATTTCGAAGATTATGGAGAATCCTGATGTTG
CCATGGCTTTCCAAATCCAAGAGTTCAAGCAGCCATCATGGATTGTGCTCAGAATCCAC
TGAGTATTGCAAAATACCAAAATGACAAGGAGGTGATGGACGTCTTCAACAAATATCAG
AACTATTCCCTGGGGTGGCAGTGGCCTTATCTCCGTGCTTAAGCAGCTATT
ATGTTACAACGATTGCATTTTGTTCTGTTTGAGTGAAGTATCAGTCAGAAGTGTGGGCT
CTGAGATGGAGTTTTCGCCCTCTGTTGCAACTCGGATGCACATGAAAACGTCGCTTCCTT
TATATAAATTCATTGCCCTTCAAATTTGTGGATTGTAACATACTTGCCTTGGCTTAC
CAGTAGTGTTTAGAGCCAATTTCAGTGTGATATTGCCAGTTCTTTATGGTTTTAGAG
TTACTTAAGCTTATTCAACTGTTATGATTTGATGAAACGGAGGAATAAAATTTTATTCA
ATAATTACTTCAATTAAAAAAAAAAAAAAAAAAAA
```

FIGURE 7

| | | |
|---|---|---|
| 1 | MQTAMKTMMNQMNTQNSQFNNPGFPTGAGAGAGSPFPFPFPPQTSPTTSPFQPQSQSSGA | (Bce44B) |
| 61 | TVDLTATKVDRPPVSKPQPTPIPPTKSIEVYKPSVVVEENKAMKEEKNYAFEDVSPEETT | (Bce44B) |
| 121 | KESPFSNYEEVSETSAPKETRLFDDVLQNGAAPANGATASDVFQSLGAGKGWAGGSVEVL | (Bce44B) |
| | PLLSAYKVFQSLGAGKGGAGLSVEAL | (Bce44A) |
| | FGSNTSDSTSSTGKSNPLLSVDAL | (Tce44) |
| 181 | EKMIEYPTFQKMLYPHLPEEMRNPESFKWVRKNPQYRQQLQDMLNNMSESGEWDKRMTET | (Bce44B) |
| | EKMMEDPTVQKMVYPHLPEEMRNPETLKWMLQNPQYRQQLQDMLNNMSGSGEWDKRMTET | (Bce44A) |
| | EKMMEDPTVQKMVYPYLPEEMRNPTTLKWMLQNPQYRQQLQDMMNNMGGNPEWDNRMMDS | (Tce44) |
| 241 | LKNFDPNSPEVKQGFDQLGLTPEEVISKIMENPDVSMAFQNPRVEAALMDCSENPMNIMK | (Bce44B) |
| | LKNFDLNSPEVKQHFDQIGLTPEEVISKIMQNPDVAMAFQNPRVQAALMECSENPMNIMK | (Bce44A) |
| | LKNFDLSSPEIKQQFDQIGLTPEEVISKIMENPDVAMAFQNPRVQAAIMDCAQNPLSIAK | (Tce44) |
| 301 | YQNDKEVMDVFNKISQLFPGLTG | (Bce44B) |
| | YQNDKEVMDVFNKISQLFPGMTG | (Bce44A) |
| | YQNDKEVMDVFNKISELFPGVAVAPCLSPSCLSSYYVTTIAFLFCLSEVSVRSVGSEMEF | (Tce44) |
| 361 | SPSVATRMHMKTSLPLYKFIALLKFCGL | (Tce44) |

FIGURE 8

ENHANCED TRANSPORT WITH A PLASTID MEMBRANE TRANSPORT PROTEIN

RELATED APPLICATION(S)

This application is a continuation-in part of the U.S. designation of PCT application PCT/CA97/00799, filed Nov. 4, 1997, which is a continuation-in-part of application U.S. Ser. No. 08/747,788, filed Nov. 14, 1996, now U.S. Pat. No. 5,919,999, the entire teachings of all of which are incorporated herein by reference.

BACKGROUND OF THE INVENTION

Plastids and mitochondria are double membrane-bound organelles found in eukaryotic cells. Chloroplasts, plastids containing the green pigment chlorophyll, are the most complex of the plant membranous organelles. Both chloroplasts and mitochondria specialize in the synthesis of ATP, using energy derived from electron transport from photosynthetic phosphorylation in chloroplasts and from oxidative phosphorylation in mitochondria.

To perform their role in the cell, plastids must continuously import all types of molecules, including proteins. The biogenesis and development of plastids require the coordinated assembly of plastidic- and nuclear-encoded proteins which are incorporated into membranes or other parts of the plastid. The process by which nuclear-encoded plastid proteins are targeted from the site of synthesis to the site of finction is mediated by a complex series of events involving a multitude of proteinaceous signals and factors located in the cytosol and the plastidic compartment. Few of these factors are known and the molecular infrastructure underlying this important and complex event is far from being understood.

Chloroplast envelope proteins play a major role in modulating the vectorial flow of molecules across the membrane, including large proteinaceous entities. The import of proteins into the plastid is a complex process requiring the close collaboration of both the outer envelope and the inner envelope membranes. Evidence for the possible existence of two distinct protein import complexes, one in each envelope membrane, is beginning to emerge from a number of recent investigations (Waegemann, K. and Soll, J. (1991) *Plant J.* 1: 149–158; Soll, J. and Waegemarn, K. (1992) *Plant J.* 2:253–256; Schnell, D. and Blobel, G. (1992) *J. Cell. Biol.* 120:103–115; Alefson, H., Waegemann, K. and Soll, J. (1994) *J. Plant Physiol.* 144:339–345; Schnell, D., et al. (1994) *Science* 266:1007–1012; Kessler, F., et al. (1994) *Science* 266:1035–1039; Wu, C., Seibert, F. S. and Ko, K. (1994) *J. Biol. Chem.* 269:32264–32271).

An important step in the characterization of the protein translocating complexes is the identification of the components involved. The identification of outer and inner plastid envelope polypeptides has been accomplished using a variety of strategies (Ma, Y., et al. (1996) *J. Cell Biol.* 134:315–327; Comwall, K. L. and Keegstra, K. (1987) *Plant Pysiol.* 85:780–785; Kaderbhai, M. A., et al. (1988) *FEBS Lett.* 232:313–316; Pain, D., et al. (1988) *Nature* 331:232–237; Schnell, D., et al. (1990) *J. Cell Biol.* 111:1825–1838; Hinz, G. and Flugge, U.-I. (1988) *Eur. J. Biochem.* 175:649–659; Soll, J. and Waegemanm, K. (1992) *Plant J.* 2:253–256; Waegemann, K., et al. (1990) *FEBS Lett.* 261:89–92; Perry, S. E. and Keegstra, K. (1994) *Plant Cell* 6:93–105; Alefson, H., et al. (1994) *J. Plant Pysiol.* 144:339–345; Schnell, D. J., et al. (1994) *Science* 266:1007–1012; Kessler, F., et al. (1994) *Science* 266:1035–1039; Wu, C., et al. (1994) *J. Biol. Chem.* 269:32264–32271; Hirsch, S., et al. (1994) *Science* 266:1989–1992; Seedorf, M., et al. (1995) *Plant J.* 7:401–411; Seedorf, M. and Soll, J. (1995) *FEBS Lett.* 367:19–22; Gray, J. C. and Row, P. E. (1995) *Trends Cell Biol.* 5:243–247). To date, these studies collectively indicate that envelope proteins with molecular masses of 21, 30, 34, 36, 44, 45, 51, 66, 70, 75 86, 97 and 100 kDa may be possible constituents of the plastid protein import apparatus; however, it is not obvious from the existing data whether some of the predicted similar sized components are identical to each other. Further, it is not known if any of the components have an active role in protein transport.

A mechanism for controlling the transport of substances into plastids could be used for modification of plastid pathways and products which occur in particular tissue types, such as the starch and fatty acid biosynthesis pathways in roots and seeds. Major drawbacks to plastid modification of this caliber, however, are the limited knowledge of genes encoding plastid transport proteins and the lack of characterization of such proteins.

Further, plastid transport mechanisms could be usefully incorporated into other organisms, especially prokaryotes. The heterologous production of protein pharmaceuticals in *Escheriehia coli* is a cornerstone of the biotechnology industry. The technology provides an attractive and viable means for the production of proteins in quantities and qualities that are otherwise expensive and difficult to obtain from natural sources.

The gene sequence and encoded protein of one plastid membrane component has been identified. Ko, K., et al. (1995) *J. Biol. Chem.* 270:28601–28608; GenBank™/EMBL Data Bank, accession no. X79091. However, no role in transport was determined for this protein.

To date, no one has reported eukaryotic transport gene function or the functioning of a transport gene from a eukaryotic organelle in prokaryotic cells. An additional transport gene in both prokaryotic and eukaryotic cells would be useful to increase translocation and expression of cellular products. Increased incorporation of proteins into membranes to elevate membrane function would also be desirable.

SUMMARY OF THE INVETION

This invention relates to a method for enhancing the transport of substances, particularly proteins, across a cellular membrane ("translocation") by means of isolated or recombinant nucleic acids encoding a plastid transport protein (Bce44B) or its functional equivalent. Nucleic acids which hybridize to the Bce44B gene are also encompassed by this invention when such hybridizing sequences encode the functional equivalent of the Bce44B protein. The present invention also relates to a method for enhancing the incorporation of substances, particularly proteins, into cellular membranes.

The cellular membranes can be those of prokaryotic or eukaryotic cells. They can include membranes of organelles, either single- or double-membrane bound organelles, as well as plasma membranes.

One object of this invention is to provide a method for the enhanced translocation and/or expression of the products of bacterial fermentation or culture. The nucleic acids described herein can be used to facilitate and increase the synthesis and secretion of products as a result of the enhancement of molecular transport in bacteria when encoded products of such nucleic acids are incorporated into the cellular membranes of bacteria.

Another object of this invention is to provide a membrane transport system which is independent of a naturally-occurring (native) transport system. Thus, prokaryotic or eukaryotic systems can be provided with selected transport mechanisms, especially systems which bypass naturally-occurring transport mechanisms such as the SecA system in *E. coli.*

In another embodiment, the DNA of this invention can be used to enhance the growth of nonhuman organisms, and to produce useful quantities of many different substances. These substances include proteins and other molecules which are translocated by cells, as well as substances which are incorporated into cell membranes of all types: i.e., plasma membranes, plastid membranes (including thylakoids), mitochondrial membranes (including cristae), Golgi membranes, endoplasmic reticula membranes, and the like.

Another object of this invention is to provide a vector comprising the DNA of SEQ ID NO:1 or a nucleic acid sequence which hybridizes to SEQ ID NO:1, and a promoter, which vector encodes membrane transport protein Bce44B, or a functional equivalent. Any hybridizing nucleic acid sequence capable of directing protein transport in a manner similar to Bce44B is included.

These vectors can be used in host cells such as prokaryotes and yeasts to enhance transport across cellular membranes. In addition, such vectors can be incorporated into the cells of nonhuman multicellular organisms to enhance translocation of substances across plasma membranes and/or organelle membranes.

Another object of this invention is the enhancement and modification of the import capability of the plastid compartment. Enhancement of protein import may increase the accumulation of all protein products in plastids, particularly in cells of seed and storage tissues. It can also boost the importation of enzymes involved in various biochemical pathways that function within the plastid. General enhancement of protein import in plastids to elevate the amount of biochemical activity in plastids and the storage of proteins and possibly other valuable products can also be achieved using the methods of this invention. Enhancements of this nature can increase product synthesis.

The same benefits can be demonstrated in bacteria using this technology so that products based on bacterial secretion and exportation are more readily accumulated, solubilized and translocated. The chimeric genes and vectors exemplified for both bacteria and plants are available for introduction into selected strains. In fact, the methods of this invention are suitable for use in all prokaryotes and eukaryotes.

This invention also provides a method whereby the activity of the Bce44B protein or its functional equivalent can be or can produce a visual plant transformation marker. Thus, use of markers which are not plant in origin, or herbicide or antibiotic resistance markers which cause concerns about their regulation or widespread use in plants can be avoided.

BRIEF DESCRIPTION OF THE DRAWINGS

FIG. 1 is a nucleic acid sequence which encodes the Bce44B protein (SEQ ID NO:1).

FIG. 2 is the amino acid sequence of the Bce44B protein (SEQ ID NO:2) encoded by SEQ ID NO:1.

FIG. 7 is a diagram of the partial Tce44 cDNA sequence (SEQ ID NO:3).

FIG. 8 is a diagram of the aligned amino acid sequences of the Bce44B, Bce44A (SEQ ID NO:5), and Tce44 (SEQ ID NO:4) proteins.

DETAILED DESCRIPTION OF THE INVENTION

Figure 3:
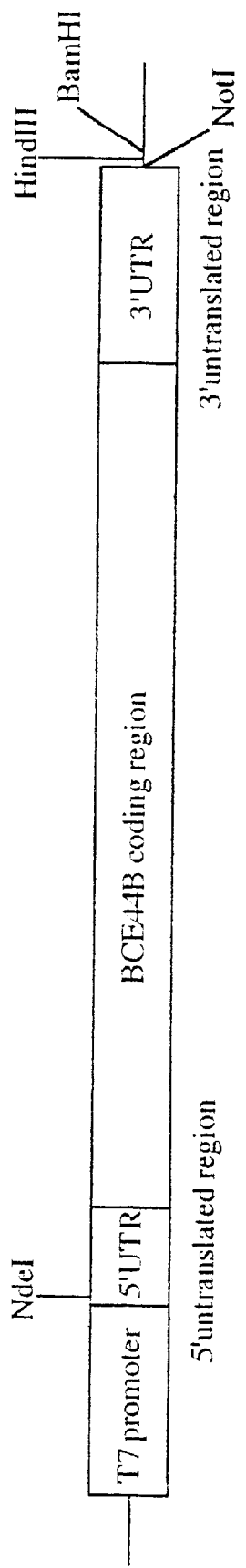
FIG. 3 is a diagram of a Bce44B expression plasmid.

The invention relates to methods using isolated and/or recombinant nucleic acids (DNA or RNA) that are characterized by (1) their ability to hybridize to (a) a nucleic acid encoding a Bce44B protein or polypeptide, such as a nucleic acid having the sequence of SEQ ID NO:1 or (b) a portion of the foregoing (e.g., a portion comprising the minimum nucleotides required to encode a functional Bce44B protein; or by (2) their ability to encode a polypeptide having the amino acid sequence of Bce44B (e.g., SEQ ID NO:2), or to encode functional equivalents thereof; e.g., a polypeptide which when incorporated into a particular membrane (such as the outer envelope of a plastid) facilitates the transport of like molecules in the same manner as Bce44B; or by (3) both characteristics. A functional equivalent of Bce44B, therefore, would have a similar amino acid sequence and similar characteristics to, or perform in substantially the same way as, a Bce44B protein. A nucleic acid which hybridizes to a nucleic acid encoding a Bce44B polypeptide such as SEQ ID NO:1, can be double- or single-stranded. Hybridization to DNA such as DNA having the sequence SEQ ID NO:1, includes hybridization to the strand shown or its complementary strand.

In one embodiment, the percent amino acid sequence similarity between a Bce44B polypeptide such as SEQ ID NO:2 and functional equivalents thereof is at least about 25% (≧25%). In a preferred embodiment, the percent amino acid sequence similarity between a Bce44B polypeptide and its functional equivalents is at least about 30% (2 30%/0). More preferably, the percent amino acid sequence similarity between a Bce44B polypeptide and its functional equivalents is at least about 40%, and still more preferably, at least about 45%.

In another embodiment, the percent amino acid sequence similarity between a Bce44B polypeptide such as SEQ ID NO:2 and functional equivalents thereof is at least about 60% (≧60%), preferably at least about 80% (≧80%), more preferably at least about 90%, and still more preferably, at least about 95%.

When specific sequences are referred to in the present invention, it is understood that these sequences include within their scope, sequences which are substantially similar to the specific sequences. Sequences are "substantially similar" when at least about 80%, preferably at least about 90% and most preferably at least about 95% of the nucleotides match (i.e., share sequence identity) over a defined length of the molecule. "Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two nucleotide or amino acid sequences are identical, then the two sequences are 50% identical; if 90% of the positions, e.g., 9 of 10 are matched, the two sequences share 90% sequence identity. By way of example, the amino acid sequences $R_{20}R_2R_8R_{11}R_6R_{15}$ and $R_9R_1R_8R_{11}R_6R_{15}$ have residues at 3 of 6 positions in common, and therefore share 50% sequence identity, while the sequences $R_{20}R_2R_8R_{11}R_6R_{15}$ and $R_1R_{14}R_{11}R_6R_{15}$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_{20}R_2R_8R_{11}R_6R_{15}$ and $R_{20}R_2R_8R_{11}R_{15}$ have 5 out of 6 position in common, and therefore share 83.3% sequence identity. Identity is often measured using sequence analysis software e.g., BLASTN or BLASTP (Altschul et al., *Nuc. Acids Res*. 25:3389402, 1997; available at http://www.ncbi.nlm.nih.gov/BLAST/). The default parameters for comparing two sequences (e.g., "Blast"-ing two sequences against each other, http://www.ncbi.nlm.nih.gov/gorf/bl2.html) by BLASTN (for nucleotide sequences) are preferred, and are: reward for match=1, penalty for mismatch=–2, open gap=5, extension gap=2. When using BLASTP for protein sequences, the default parameters are preferred, and are: reward for match=0, penalty for mismatch=0, open gap=11, and extension gap=1. The similar or homologous sequences can also be identified by using, for example, the GCG (Genetics Computer Group, Program Manual for the GCG Package, Version 7, Madison, Wis.) pileup program.

Sequences that are "substantially similar" include any nucleotide sequence which is altered to contain a substitution, deletion, or addition of nucleotides compared to the sequences of this invention, especially substitutions which rely on the degeneracy of the genetic code, and which have similar characteristics (i.e., finction). "Substantially similar" polynucleotide sequences, therefore, include those sequences that differ in nucleotide sequence, but which produce homologous polypeptides.

Two polypeptide sequences can differ from each other by conservative substitutions, which include substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one nonpolar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may be called "sequence homologs." Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutaric acid; asparagine, glutamine; serine, threonine; lysine, arginine; and phenylalanine, tyrosine.

Isolated and/or recombinant nucleic acids meeting these criteria comprise nucleic acids having sequences identical to sequences of naturally occurring Bce44B genes and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

"Stringency conditions" permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences may be less similar to each other if they hybridize under moderate stringency conditions. Still less similarity is needed for two sequences to hybridize under low stringency conditions. Hybridization of oligonucleotides is described at page 14.15 in Sambrook, et al. (1989) *Molecular Cloning: A Laboratory Manual*, Cold Spring Harbor Laboratory, Cold Spring Harbor, N.Y., the entire contents of which are hereby incorporated by reference in their entirety. By varying the hybridization conditions from a stringency level at which no hybridization occurs, to a level at which hybridization is first observed, conditions can be determined at which a given sequence will hybridize specifically to those sequences that are most similar to it.

High stringency hybridization procedures can (1) employ low ionic strength and high temperature for washing, such as 0.015 M NaCl/0.0015 M sodium citrate, pH 7.0 (0.0×SSC) with 0.1% sodium dodecyl sulfate (SDS) at 50° C.; (2) employ during hybridization 50% (vol/vol) formamide with 5×Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

"High stringency conditions" can also employ hybridization at either (1) 1×SSC (10×SSC=3 M NaCl, 0.3 M $Na_3$-citrate-$2H_2O$ (88 g/liter), pH to 7.0 with 1 M HCl), 1% SDS (sodium dodecyl sulfate), 0.1–2 mg/ml denatured salmon sperm DNA at 65° C., (2) 1×SSC, 50% formamide, 1% SDS, 0.1–2 mg/ml denatured salmon sperm DNA at 42° C., (3) 1% bovine serum albumen (fraction V), 1 mM $Na_2$·EDTA, 0.5 M $NaHPO_4$ (pH 7.2) (1 M $NaHPO_4$=134 g $Na_2BPO_4 \cdot 7H_2O$, 4 ml 85% $H_3PO_4$ per liter), 7% SDS, 0.1–2 mg/ml denatured salmon sperm DNA at 65° C., (4) 50% formamide, 5×SSC, 0.02 M Tris-HCl (pH 7.6), 1×Denhardt's solution (100x=10 g Ficoll 400, 10 g polyvinylpyrrolidone, 10 g bovine serum albunmin (fraction V), water to 500 ml), 10% dextran sulfate, 1% SDS, 0.1–2 mg/ml denatured salmon sperm DNA at 42° C., (5) 5×SSC, 5×Denhardt's solution, 1% SDS, 100 µg/ml denatured salmon sperm DNA at 65° C., (6) 5×SSC, 5×Denhardt's solution, 50% formamide, 1% SDS, 100 µg/ml denatured salmon sperm DNA at 42° C., with high stringency washes of either (1) 0.3–0.1×SSC, 0.1% SDS at 65° C., or (2) 1 mM $Na_2EDTA$, 40 mM $NaHPO_4$ (pH 7.2), 1% SDS at 65° C., or (7) prehybridization in 50% formamide, 5×SSC, 25 mM potassium phosphate buffer (pH 7.4), 5×Denhardt's, and 50 µg/ml denatured salmon sperm DNA for 4–12 hours at 37° C., which is followed by hybridization for 12–24 hours at 37° C. and washing in 2×SSC containing 0.1% SDS, at 55° C. The above conditions are intended to be used for DNA-DNA hybrids of 50 base pairs or longer. Where the hybrid is believed to be less than 16 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 16 to about 49 base pairs in length, the $T_m$ in ° C.=(81.5° C.+16.6($\log_{10}$M)+0.41(% G+C)−0.61 (% formamide)−500/L), where "M" is the molarity of monovalent cations (e.g., $Na^+$), and "L" is the length of the hybrid in base pairs.

"Moderate stringency conditions" can employ hybridization at either (1) 4×SSC, (10×SSC=3 M NaCl, 0.3 M $Na_3$-citrate-$2H_2O$ (88 g/liter), pH to 7.0 with 1 M HCl), 1% SDS (sodium dodecyl sulfate), 0.1–2 mg/ml denatured salmon sperm DNA at 65° C., (2) 4×SSC, 50% formamide, 1% SDS, 0.1–2 mg/ml denatured salmon sperm DNA at 42° C., (3) 1% bovine serum albumen (fraction V), 1 mM $Na_2$·EDTA, 0.5 M $NaHPO_4$ (pH 7.2) (1 M $NaHPO_4$=134 g $Na_2HPO_4 \cdot 7H_2O$, 4 ml 85% $H_3PO_4$ per liter), 7% SDS, 0.1–2 mg/ml denatured salmon sperm DNA at 65° C., (4) 50% formamide, 5×SSC, 0.02 M Tris-HCl (pH 7.6), 1×Denhardt's solution (100x=10 g Ficoll 400, 10 g polyvinylpyrrolidone, 10 g bovine serum albumin (fraction V), water to 500 ml), 10% dextran sulfate, 1% SDS, 0.1–2 mg/ml denatured salmon sperm DNA at 42° C., (5) 5×SSC, 5×Denhardts solution, 1% SDS, 100 µg/ml denatured salmon sperm DNA at 65° C., or (6) 5×SSC, 5×Denhardt's solution, 50% formamide, 1% SDS, 100 µg/ml denatured salmon sperm DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 16 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 16 to about 49 base pairs in length, the $T_m$ in ° C.=(81.5° C.+16.6($\log_{10}$M)+0.41(% G+C)−0.61 (% formamide)−500/L), where "M" is the molarity of monovalent cations (e.g., $Na^+$), and "L" is the length of the hybrid in base pairs.

"Low stringency conditions" can employ hybridization at either (1) 4×SSC, (10×SSC=3 M NaCl, 0.3 M $Na_3$-citrate·$2H_2O$ (88 glitter), pH to 7.0 with 1 M HCl), 1% SDS (sodium dodecyl sulfate), 0.1–2 mg/ml denatured salmon sperm DNA at 50° C., (2) 6×SSC, 50% formamide, 1% SDS, 0.1–2 mg/ml denatured salmon sperm DNA at 40° C., (3) 1% bovine serum albumen (fraction V), 1 mM $Na_2$·EDTA, 0.5 M $NaHPO_4$ (pH 7.2) (1 M $NaHPO_4$=134 g $Na_2HPO_4 \cdot 7H_2O$, 4 ml 85% $H_3PO_4$ per liter), 7% SDS, 0.1–2 mg/ml denatured salmon sperm DNA at 50° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured salmon sperm DNA at 40° C., (5) 5×SSC, 5×Denhardt's solution, 1% SDS, 100 µg/ml denatured salmon sperm DNA at 50° C., (6) 5×SSC, 5×Denhardt's solution, 50% formamide, 1% SDS, 100 µg/ml denatured salmon sperm DNA at 40° C., with low stringency washes of either 2×SSC, 0.1% SDS at 50° C., or (2) 0.5% bovine serum albumin (fraction V), 1 mM $Na_2EDTA$, 40 mM $NaBPO_4$ (pH 7.2), 5% SDS, or (7) prehybridization in 25% formamide, 5×SSC, 25 mM potassium phosphate buffer (pH 7.4), 5×Denhardt's, and 50 µg/ml denatured salmon sperm DNA for 4–12 hours at 37° C., which is followed by hybridization for 12–24 hours at 37° C. and washing in 2×SSC containing 0.1% SDS, at 42° C. The above conditions are intended to be used for DNA-DNA hybrids of 50 base pairs or longer. Where the hybrid is believed to be less than 16 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 16 to about 49 base pairs in length, the $T_m$ in ° C.=(81.5° C.+16.6($\log_{10}$M)+0.41(% G+C)−0.61 (% formamide)−500/L), where "M" is the molarity of monovalent cations (e.g., $Na^+$), and "L" is the length of the hybrid in base pairs.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson (1991) *Methods in Enzymology*, 200:546–556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding a Bce44B polypeptide, such as the nucleic acid depicted as SEQ ID NO:1, (b) the complement of SEQ ID NO:1, (c) or a portion of (a) or (b) (e.g., under high or moderate stringency conditions), may further encode a protein or polypeptide having at least one function characteristic of a Bce44B polypeptide, such as translocation activity (e.g., transport of β-lactamase across a bacterial cell membrane), or binding of antibodies that also bind to non-recombinant Bce44B. The catalytic or binding function of a protein or polypeptide encoded by the hybridizing nucleic acid may be detected by standard enzymatic assays for activity or binding (e.g., assays which measure the binding of a transit peptide or a precursor, or other components of the translocation machinery). Enzymatic assays, complementation tests, or other suitable methods can also be used in procedures for the identification and/or isolation of nucleic acids which encode a polypeptide such as a polypeptide of the amino acid sequence SEQ ID NO:2, or a functional equivalent of this polypeptide. The antigenic properties of proteins or polypeptides encoded by hybridizing nucleic acids can be determined by immunological methods employing antibodies that bind to a Bce44B polypeptide such as immunoblot, immunoprecipitation and radioimmunoassay. PCR methodology, including RAGE (Rapid Amplification of Genomic DNA Ends), can also be used to screen for and detect the presence of nucleic acids which encode Bce44B-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

The nucleic acids described herein are used in the methods of the present invention for production of proteins or polypeptides which are incorporated into cellular membranes and which facilitate transport of substances across these membranes or incorporate these substances into the membrane. The "substances" can be proteinaceous molecules, such as proteins, peptides (including polypeptides), and molecules with peptide bonds, or can be nonpeptide compounds. In one embodiment, DNA containing all or part of the coding sequence for a Bce44B polypeptide, or DNA which hybridizes to DNA having the sequence SEQ ID NO:1, is incorporated into a vector for expression of the encoded polypeptide in suitable host cells. The encoded polypeptide consisting of Bce44B or its functional equivalent is capable of translocating substances, such as those described above. The term "vector" as used herein refers to a nucleic acid molecule capable of transporting another nucleic acid to which it has been linked. A vector, therefore, includes a plasmid or viral DNA molecule into which another DNA molecule can be inserted without disruption of the ability of the molecule to replicate itself. The terms "translocating" or "translocation" mean the transport of substances across at least one cellular membrane from one part of the cell to another or into or out of the cell or organelle (i.e., import or secret) or even into a periplasmic space (i.e., export) as that found in *E. coli* between the inner and outer membranes.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M. et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewiaker et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:1. For example, an antisense nucleic acid or oligonucleotide can be complementary to a target nucleic acid having the sequence shown as the strand of the open reading frame of SEQ ID NO:1 or nucleic acid encoding a functional equivalent of Bce44B, or to a portion of these nucleic acids sufficient to allow hybridization. A portion, for example, a sequence of 16 nucleotides could be sufficient to inhibit expression of the protein. Or, an antisense nucleic acid or oligonucleotide complementary to 5' or 3' untranslated regions, or overlapping the translation initiation codon (5' untranslated and translated regions), of the Bce44B gene or a gene encoding a functional equivalent can also be effective. In another embodiment, the antisense nucleic acid is wholly or partially complementary to and can hybridize with a target nucleic acid which encodes a Bce44D polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding Bce44B or its functional equivalent. Frank-Kamenetskii, M. D. and Mirkin, S. M. (1995) *Ann. Rev. Biochem.* 64:65–95. Such oligonucleotides of the invention are constructed using the base-pairing rules of triple helix formation and the nucleotide sequence of the gene or MRNA for Bce44B. These oligonucleotides can block Bce44B-type activity in a number of ways, including prevention of transcription of the Bce44B gene or by binding to mRNA as it is transcribed by the gene.

Co-suppression refers to the overexpression of an endogenous or an introduced gene (transgene) wherein the extra copies of the gene result in the coordinate silencing of the endogenous gene as well as the transgene, thus reducing or eliminating expression of the trait. This technology can be used to limit transport of substances across membranes. See, for example, Jorgensen et al., U.S. Pat. Nos. 5,034,323 and No. 5,283,184.

An alternative strategy to reduce the amount of Bce44B or its functional equivalent can be devised based on the use of "dominant-negative" mutant proteins. Certain types of mutations can be introduced into regulatory proteins that render them non-functional, but permit the mutant proteins to compete with the native proteins for their targets, which may include other protomers of a multimeric protein. Such competition by a non-functional protein means that overexpression of the mutant protein can be used to suppress the activity of the native protein. In plants, dominant-negative strategies have been used successfully with other types of regulatory proteins. See, Boylan, M. et al. (1994) *Plant Cell* 6:449–460; Rieping, M. et al. (1994) *Plant Cell* 6:1087–1098; and Hemerly, A. et al. (1995) *EMBO J.* 14:3925–3936.

Those of skill in the art can appreciate the numerous examples wherein these strategies can result in commercial advantages in plants and other organisms. The following are several examples, not intended to be limiting, which describe the type of modification of plants that are possible using directed, tissue-specific expression. Seed or pollen development or production can be impaired or inhibited. This is especially useful where a company does not want seeds of a valuable crop, generated and harvested by competitors. The incorporation of truncated or mutant versions of Bce44B into organelle membranes could disturb transport to the extent that an antisense-type of inhibition occurs in a particular tissue, for example, resulting in male sterility. Expression in pollen which disrupts or impairs its function could be especially useful to prevent escape of transgenic materials from crops. Transfer of inhibitory genetic material to wild populations of unwanted plants could produce herbicidal effects and valuable weed control. This type of population control can extend to aquatic organisms, such as the dinoflagellates which produce red tides, or blue-green algae which are responsible for toxic blooms in freshwater systems. Even more useful, yields of crops harvested for vegetative materials could be increased by impairing the investment of energy in flower and seed production.

The invention also relates to methods using the proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "substantially purified" have been isolated and purified, such as by one or more steps usually including column chromatography, differential precipitation, or the like, to a state which is at least about 10% pure. Proteins or polypeptides referred to herein as "recombinant" are proteins or polypeptides produced by the expression of recombinant nucleic acids.

This invention provides a method for enhancing protein or peptide transport across a cellular membrane by incorporating an isolated nucleic acid encoding a plastid-derived transport protein, Bce44B (SEQ ID NO:1) or its functional equivalent into a cell or organism and maintaining the cell or organism under conditions appropriate for expression of the Bce44B protein or its functional equivalent.

The constructs and methods described herein can be applied to all types of plants and other photosynthetic organisms, including, but not limited to: angiosperms (monocots and dicots), gymnosperms, spore-bearing or vegetatively-reproducing plants and the algae, including the cyanophyta (blue-green algae). Similar sequences have been found in tomato, and can be found in species closely related to *Brassica napus* such as broccoli, cabbage, brussels sprouts, and mustard, and can be found in members of the Dicotyledoneae and the Monocotyledoneae. For example, a tomato sequence (Tce44, SEQ ID NO:3, FIG. 7) and a second Brassica sequence (Bce44A, SEQ ID NO:4, FIG. 8) have been isolated.

Particularly preferred plants, either as sources of the polynucleotides for building such constructs, or as targets for transformation with the constructs, are those plants which provide commercially-valuable crops, such as grains (e.g. maize, wheat, barley, oats, rice, rye, quinoa, amaranth), starchy root crops (e.g., potato, sweet potato, yam, cassava), oil crops (e.g., canola, maize, peanut, soybean, sunflower, coconut), sugar crops (e.g., sugar cane and sugar beet), legumes (e.g. bean, soybean, pea, chickpea), vegetables (e.g., tomatoes, broccoli, carrot, pea, lettuce), fruits (e.g., apple, pear, plum, banana, orange, lemon), horticultural species (e.g. rose, chrysanthemum), and species for the production of secondary metabolites (e.g., Digitalis, autumn crocus and other medicinal plants, spice plants such as vanilla or cinnamon, dye plants such as indigo, fiber plants such as cotton).

Further, the constructs and methods of this invention can be adapted to any plant part, protoplast, or tissue culture wherein the tissue is derived from a photosynthetic organism. The term "plant part" is meant to include a portion of a plant capable of producing a regenerated plant. Preferable plant parts include roots and shoots and meristematic portions thereof. Other plant parts encompassed by this invention are: leaves, flowers, seeds, epicotyls, hypocotyls, cotyledons, cotyledonary nodes, explants, pollen, ovules, meristematic or embryonic tissue, protoplasts, and the like. Transgenic plants can be regenerated from any of these plant parts, including tissue culture or protoplasts, and also from explants. Methods will vary according to the species of plant.

The methods of the present invention can be used to enhance transport of molecules across any type of cellular membrane. This includes not only one or both of the double membranes of chloroplasts, mitochondria, nuclei and many bacteria, but also plasma membranes, thylakoids, cristae, vesicular membranes, golgi membranes, membranes which comprise the endoplasmic reticulum, and the like. In fact, artificially-made membranes or vesicles can also can also work when the appropriate proteins of the invention are incorporated, and be useful, for example, to sequester translocated compounds.

For example, it would be desirable to increase dye transport into the vacuole of cells in plants where color is commercially important, such as in dye plants (e.g., indigo) and floricultural crops (e.g., rose). Similarly, it would be desirable to increase the transport of secondary metabolites into the vacuole in field-grown medicinal plants such as autumn crocus or Digitalis, or out of the cell entirely in commercial suspension cultures of *Mucona prunriens* (which produces L-DOPA), or Cinchona (which produces quinine).

It is also understood that the transport proteins of the present invention can function to transport molecules across membranes of all types of cells, preferably plant cells, and in cell lines of organisms, preferably plants. The cells may comprise single-celled prokaryotic organisms; i.e., the bacteria and cyanobacteria (blue-green algae). Alternatively, the cells can be animal-like, plant-like or fungal-like protists (single-celled eukaryotic organisms). Multicellular nonhuman organisms, including animals and all members of the fungi and plant kingdoms, are also suitable for application of the methods of this invention. Cell lines incorporating the enhanced transport methods of this invention can be derived from any of these eukaryotic organisms.

In addition to transport of molecules into and out of organelles and cells, the methods of the present invention can be used to incorporate proteins and other molecules into membranes. Like many proteins that form part of a membrane structure and facilitate transfer of molecules through the membrane, these proteins are also capable of integrating substances into membrane structure.

The invention described herein demonstrates for the first time that the Bce44B protein is an important membranous protein transport component which not only can translocate substances across membranes, but can incorporate molecules into membranes as well. The transported substances can be proteins, molecules containing peptide bonds, or even nonproteinaceous molecules.

A novel aspect of this invention is the finding that this protein will incorporate and function in any membrane, including the inner and outer membranes of prokaryotes such as *E. coli*, not just the chloroplast envelope where it occurs naturally. Even more surprising is the discovery that the protein transports substances out of the bacterial cell; whereas, in a plastid, transport of proteins occurs from the cytosol into the intraorganellar sites of the organelle. That Bce44B is effective by itself, without requiring additional introduction of a multicomponent transport assembly, is both unusual and advantageous. Further, this is the first time a eukaryotic gene encoding a membranous protein transport component has been incorporated into a prokaryote and the protein expressed with functional activity.

In one embodiment, therefore, translocation of molecules is further enhanced by elevating the efficiency of molecular translocation and/or by creating additional pathways for transport via the introduction and expression of a central component of the plant plastid protein import apparatus in bacteria. The natural role of Bce44B in plants is to assist in the import of proteins into the plastid compartment. Expression of Bce44B in bacteria appears to stimulate a higher, more efficient level of protein translocation. While not to be limited by theory, these higher levels probably result from acceleration of the protein translocation process or from the addition of more pathways for transport. Further, the enhancement is probably stable because the newly introduced protein is not recognized as being bacterial in origin, thereby reducing the possibility of down-regulation. This technology is novel because the enhancement of bacterial protein translocation is caused by a plant protein component and because the activity of this component also results in an elevation of protein expression. Together, these two features make a novel and significant impact on the ultimate levels of translocated proteins. The enhancement of foreign protein production and translocation can be achieved by stably introducing the desired gene construct into an *E. coli* strain expressing the plant protein component. The same method can also enhance transport into plastids and other organelles of plants at levels and/or in a manner which is not found in the naturally-occuring organism.

The chloroplast protein importation apparatus and Bce44B:

The complex nature of protein translocation mechanisms observed in other membranous systems, such as the mitochondrion and the endoplasmic reticulum, suggests that there is most likely a significant number of plastid envelope components that need to be identified and characterized in detail. One major strategy for identifing and studying putative or possible components of the protein translocation apparatus is to isolate cDNA clones that encode all types of chloroplast envelope proteins and then to systematically sort out the identity and/or function of the clones. This approach allows skilled artisans to circumvent the technical problems and limitations of purifying small quantities of authentic proteins from the envelope.

To isolate the compounds for the methods of this invention, a cDNA clone encoding a 44 kDa envelope protein with unusual features was isolated and characterized. Ko et al. (1995) *J. Biol. Chem.* 270:28601. The 44 kDa polypeptide encoded by this cDNA insert is a member of the Com44/Cim44 chloroplast envelope proteins (Wu et al. (1994) *J. Biol. Chem.* 269:32264). Although, these proteins have been found in close proximity to a partially translocated chimeric precursor protein, any role in the translocation process was heretofore unknown. A similar method was employed to isolate the sequence from tomato FIG. 7, CDHA, (SEQ ID NO:3, and FIG. 8, amino acid, (SEQ ID NO:4), and a second Brassica gene (SEQ ID NO:4). The aligned sequences are depicted in FIG. 8.

Specific antibodies were raised against the 44 kDa protein and used to determine the location of the immunologically-related polypeptides in the chloroplast envelope. The combined data from nucleotide sequencing, and RNA and protein blot analyses indicated the existence of multiple forms of the 44 kDa envelope protein. Depending on the plant species examined, immunologically-related protein bands with molecular masses of 42 to 46 kDa were observed. Organelle subfractionation, protease treatment and immunomicroscopy studies together provided an indication that the immunologically-related proteins could be present in both the outer and inner envelope membranes. Co-migration of the product synthesized from the cDNA insert with a 44 kDa immunoreactive band of the chloroplast envelope, and the in vitro import results, together suggest that the in vitro synthesized 44 kDa protein is targeted to the envelope membrane without any further processing.

Parallelism of chloroplast and bacterial protein translocation systems:

Nuclear-encoded chloroplast precursor proteins are synthesized in the cytosol and then targeted to the organelle. The translocation of precursor proteins into the chloroplast is a highly complex process involving a multitude of components such as energy (mainly in the form of ATP), transit signals, proteinaceous envelope membrane factors, processing peptidases and chaperones. These components are responsible for facilitating various steps of the import process which encompasses unfolding, specific binding to receptors on the outer envelope, translocation across the two envelope membranes, and precursor maturation (Keegstra, K. and Olsen, L. J. (1989) *Annu. Rev. Plant Physiol. Plant Mol. Biol.* 40:471). A number of these chloroplastic components possess features in common with factors involved in the translocation of precursor proteins across the two bacterial cytoplasmic membranes and have indeed been demonstrated to be interchangeable to a certain extent. The transit signals of chloroplast precursor proteins can be recognized by the bacterial protein export machinery and transported into the periplasmic space, where processing to the correct mature molecular size occurs (Seidler, A. and Michel, H. (1990) *EMBO J.* 9:1743). In many cases, the processing sites of chloroplastic transit signals follow the bacterial −3, −1 rule and are readily cleaved by *E. coli* signal peptidase (Halpin et al. (1989) *EMBO J.* 8:3917). In addition to the prokaryotic nature of the thylakoid lumen-targeting signal, the 33 kDa subunit of the oxygen-evolving complex and plastocyanin traverse the thylakoid membrane via an azide-sensitive pathway resembling bacterial azide-sensitive protein export (Cline et al. (1993) *EMBO J.* 12:4105; Knott and Robinson (1994) *J. Biol. Chem.* 269:7843). Plastidic counterparts of the bacterial components GroEL, DnaK, SecA and SecY are present at internal sites in the organelle (Gutteridge and Gatenby (1995) *Plant Cell* 7:809; Nohara et al. (1995) *FEBS Lett.* 364:305; Reith and Munholland (1993) *Plant Cell* 5:465; Laidler et al. (1995) *J. Biol. Chem.* 270:17664) and in cases concerning GroEL, Srp54 and SecA counterparts, have been demonstrated to fimction in a very similar manner (Yuan et al. (1994) *Science* 266:796; Gutteridge and Gatenby (1995) *Plant Cell* 7:809; Makai et al. (1994) *J. Biol. Chem.* 269:31338; Franklin and Hoffinan (1993) *J. Biol. Chem.* 268:22175; Li et al. (1995) *Proc. Natl. Acad. Sci. USA* 92:3789).

The apparent parallelism of the chloroplastic and bacterial protein translocation systems suggests that other plastidic components are interchangeable and functional to some degree in a bacterial environment. It also suggests that translocation systems of a similar nature are present in membranes of other eukaryotic organelles and in cyanobacterial cells. Thus the methods of this invention provide a very useful and novel approach for studying different aspects of the interchanged membrane transport components. This idea was tested by introducing and expressing the recently identified component of the chloroplast protein import apparatus, Bce44B, in bacteria. Bce44B was previously found to be in close physical proximity to partially translocated chimeric precursor proteins and is a member of the Com44/Cim44 envelope polypeptides (Wu, C. et al. (1994) *J. Biol. Chem.* 269:32264; Ko et al. (1995) *J. Biol. Chem.* 270:28601). Introduction and expression of Bce44B was accomplished by subdloning the corresponding cDNA sequence into a T7 promoter-containing plasmid vector (pGEM11Z) and JM109(DE3), a bacterial strain used for overexpressing proteins. See Example 6. Expression of Bce44B in bacteria gave rise to a multiple protein pattem.

The largest band corresponded to the full length Bce44B protein with a relative molecular mass of 44 kDa. There were smaller protein bands observed which were most likely derived from a combination of post-translational degradation, since most of them co-fractionated exclusively with the inclusion bodies and the cytosol, and translation-related events such as internal translation initiations or premature termination of translation. Full length Bce44B co-fractionated primarily with cytoplasmic membranes and crude inclusion bodies. Right-side-out (RSO) and inside-out vesicles (ISO) of bacterial cells were prepared and treated with thermolysin (Kim, Y. J., and Oliver, D. B. (1994) *FEBS Lett.* 339:175; Kim, Y.J. et al. (1994) *Cell* 78:845) to further determine the nature of the association of Bce44B with the cytoplasmic membranes. See Example 10 through Example 12.

A portion of the membrane-associated Bce44B proteins in both types of vesicles were resistant to post-fractionation protease treatments and became sensitive only in the presence of detergents, e.g., Triton X-100. Vesicles that received a mock protease treatment did not exhibit any Bce44B degradation. The protected portion of the membrane-associated Bce44B proteins is most likely protected from protease degradation by the bacterial membrane, and appears to be associated in a manner similar to its natural environment, the chloroplast envelope. These results indicate that the bacterial protein translocation machinery is capable of recognizing Bce44B and actively integrates it into the cytoplasmic membranes. The membrane-associated Bce44B proteins were present in both the outer membrane and the inner membrane. A large portion of Bce44B fractionated with the outer membrane and a smaller level was found in the inner membrane. The dual nature of the distribution of Bce44B in the bacterial plasma membrane resembles the situation observed in the chloroplast envelope, except that it is opposite to the inner/outer envelope pattern of distribution. The directionality of the Bce44B distribution pattern may reflect the direction of protein translocation, namely outward in bacteria and inward in chloroplasts.

Determination of the function of Bce44B in bacteria using alkaline phosphatase as a monitor:

The directionality of the distribution of Bce44B in the cytoplasmic membrane and the capability of the bacterium to recognize and integrate Bce44B into the membrane raised the possibility that Bce44B may be functional as a foreign component of the bacterial protein transport apparatus. Functionality of Bce44B was therefore assessed by monitoring two transported bacterial proteins, alkaline phosphatase and , β-lactamase. Alkaline phosphatase is a single copy gene and is transported into the periplasm upon induction by phosphate starvation (50 $\mu$M) (Torriani et al. (1960) *Biochim. Biophys. Acta*. 38:460). The growth characteristics of Bce44B-containing bacteria were compared to those of a strain expressing Oee1-Dhfr, a chimeric chloroplast protein precursor. The expression vector used in the Oee1-Dhfr transformed strain was the same as the one in the Bce44B transformed cells. Growth was monitored in M9 minimal media with growth-permissive phosphate levels or with low phosphate levels (50 $\mu$M).

The Bce44B-containing cells displayed a growth curve distinct from the Oee1-Dhfr-containing cells. Bce44B cells displayed double peaks during growth in low phosphate, whereas Oee1-Dhfr cells exhibited only one. Bce44B-expressing cells harvested at the time corresponding to the two growth peaks contained a higher level of processed alkaline phosphatase relative to the Oee1-Dhfr-expressing cells. The amount of processed alkaline phosphatase reflects changes in protein translocation activity. Even though phosphate is a nutrient vital for the survival of the bacterium and although there is most likely a variety of mechanisms operating to allow survival under phosphate starvation, the data show that the presence of Bce44B contributes to enhanced levels of alkaline phosphatase in the periplasm, which in turn allows the cells to grow further by releasing more phosphate from limited sources.

Measurement of protein translocation enhancement using β-lactamase as a transport marker:

The enhancement of protein translocation was further investigated using the plasmid-borne multicopy gene, β-lactamase. See Example 14. β-lactamase protein levels are much higher than induced alkaline phosphatase making this system a more sensitive monitor of protein translocation without the complications posed by low phosphate induction. Like alkaline phosphatase, β-lactamase is translocated into the periplasm, where it detoxifies the antibiotic ampicillin, thereby conferring ampicillin-resistance to cells. Because the level of antibiotic resistance conferred also reflects the level of protein transport activity, the level of ampicillin resistance was determined for Bce44B expressing cells and compared to that of Oee1-Dhfr-expressing cells on solid agar media containing increasing concentrations of ampicillin. The plasmid copy numbers were determined to be the same in both strains (approximately 750–800) so that copy number did not contribute to differences in expression of β-lactamase. The Bce44B-expressing cells formed colonies with ampicillin concentrations as high as 3 mg/ml, whereas Oee1-Dhfr-expressing cells could not form colonies beyond 1 mg/ml.

The higher level of antibiotic resistance displayed by the Bce44B-expressing cells was reflected in the enhanced level of transported β-lactamase. Immunoblot analysis of cells grown for four hours in media containing ampicillin concentrations from 50 μg to 3 mg/ml showed that the level of processed β-lactamase is higher on a per cell basis in Bce44B-expressing cells than in Oee1-Dhfr-expressing cells. These data demonstrate that Bce44B enhances the level of '3-lactamase translocation, permitting a higher level of antibiotic resistance.

Chemical cross-linning analysis:

Direct involvement of Bce44B in the protein translocation process was confirmed by two different methods: chemical cross-linking/co-immunoprecipitation and azide sensitivity. If the integrated form of Bce44B is physically involved in protein translocation, it is probable that the cytoplasmic membrane form of Bce44B is in close physical proximity to translocating β-lactamase. The chemical cross-linking/co-immunoprecipitation results indicated that the two proteins do appear to be in close physical proximity. See Example 16. Bce44B- and Oee1-Dhfr-expressing cells were grown to mid-logarithmic phase and harvested for the preparation of spheroplasts. Washed spheroplasts were subjected to chemical cross-linking with EDAC (1-ethyl-3-(3-dimethylaminopropyl)carbodiimide) and the cross-linked complexes were analyzed by immunoblotting with antibodies against Bce44B and β-lactamase. A higher molecular sized cross-linking-generated band of approximately 70 kDa immunoreacted with both antibodies. Bands of this nature were not observed in the absence of chemical cross-linker or in the Oee1-Dhfr-expressing cells.

Cross-linked complexes between β-lactamase and another cytoplasmic membrane protein, Tet, were also not observed in tetracycline-resistant bacterial cells. Tetracycline resistance is due to the presence of a proteinaceous cytoplasmic membrane efflux pump, Tet.

The estimated molecular mass of the cross-linked complex suggests that it likely comprises one each of β-lactamase and Bce44B. These results indicate that β-lactamase is in close physical proximity to Bce44B during translocation, implicating the role of Bce44B in the bacterial protein translocation process.

Sodium azide sensitivity analysis:

Sodium azide is a potent inhibitor of bacterial SecA activity, blocing SecA-dependent protein transport in a rapid manner (Oliver et al. (1990) *Proc. Natl. Acad. Sci. USA* 87:8227). Both alkaline phosphatase and β-lactamase are known to utilize this pathway for transport. On the other hand, the translocation of proteins across the chloroplast envelope is not affected by this level of azide, even though the translocation of a subset of proteins across the thylakoid membrane is azide-sensitive (Knott and Robinson (1994) *J. Biol. Chem.* 269:7843.). Therefore the Bce44B-expressing cells were tested for azide sensitivity to assess whether protein translocation in these cells has been altered by Bce44B such that it resembles the chloroplastic protein import system. The level of β-lactamase was monitored for 2 hours in the presence of 0.5 mM sodium azide, a concentration that partially inhibits SecA activity in bacteria. Parallel experiments were conducted without sodium azide. Higher levels of transported β-lactamase were observed in the Bce44B-expressing cells than in the Oee1-Dhfr-containing cells at all time points in the absence of azide. In the presence of sodium azide, the Oee1-Dhfr-expressing cells displayed increasing amounts of the precursor form of β-lactamase and a concomitant decrease in the level of the mature transported form as incubation time progressed. The pattern of β-lactamase accumulation was different in the Bce44B-expressing cells where both precursor and mature forms of β-lactamase increased during the two hours, suggesting that Bce44B can partially compensate for the azide-impaired SecA-dependent protein transport pathway.

Complementation analysis of a temperature-sensitive secA bacterial mutant with Bce44B:

The effects of Bce44B on β-lactamase transport were further tested in a temperature-sensitive secA (secAts) mutant bacterial strain (MM52, a gift from Dr. Jon Beckwith, Harvard Medical School, Boston Mass.) to provide further evidence that the expressed Bce44B component affected protein translocation in bacteria and that the protein transport enhancement was not due solely to the upregulation of the existing bacterial transport machinery such as SecA. See Example 17. The defective protein translocation phenotype in MM52 appears primarily when cells are subjected to temperatures above 30° C. Protein translocation slows down and comes to a halt upon shifting to temperatures above 30° C. This defect is manifested in the gradual accumulation of β-lactamnase precursors with a concomitant reduction in the level of the transported mature form of the enzyme. The cause of this defect is due to the temperature-sensitive expression of the main regulatory component of the bacterial protein translocation machinery, SecA. Effects on protein transport can then be monitored in this strain by tracking the β-lactamase profiles at permissive and non-permissive temperatures.

The same Bce44B gene construct and control Oee1-Dhfr plasmid were introduced into MM52 and its wild type counterpart strain MC4100 (containing the wild-type SecA) via electroporation. The role of Bce44B in protein translocation was assessed as before using three different criteria: 1) the level of antibiotic resistance conferred; 2) the profile of transported versus precursor β-lactamase at permissive and non-permissive temperatures; and 3) the level of sensitivity of protein transport to sodium azide.

The level of antibiotic resistance conferred can reflect the level of protein transport activity; therefore the level of ampicillin resistance was again determined for these strains in the same manner as described above. Each of the strains MM52-Bcet4B, MM52-Oee1-Dhfr, MC4100-Bce44B, and MC4100-Oee1-Dhfr were plated out on solid agar media containing increasing concentrations of ampicillin. The plasmid copy numbers were determined to be similar in all strains and were not predicted to contribute to differences in the expression of β-lactamase. MM52-Bce44B-expressing cells were able to form colonies at ampicillin concentrations up to 3 mg/ml whereas MM52-Oee1-Dhfr-expressing cells were not able to form colonies beyond 1 mg/ml ampicillin when grown at 30° C., the permissive temperature. The results for the MC4100-Bce44B and MC4100-Oee1-Dhfr strains were similar to those for the MM52-based strains except that MM52 cells required 48 hours to form colonies versus the 16 hours needed for the MC4100-based strains. The MM52-based strains were not able to form colonies at 37° C. whereas the MC4100-based ones did.

The MM52 strain, although it is capable of growing at 30° C., also showed a reduced level of protein translocation at the permissive temperature and a much lower level at the non-permissive temperature of 37° C. Therefore temperature shift experiments were conducted to assess the effects of Bce44 on protein translocation at permissive and non-permissive temperatures. As described above, the level of processed versus precursor β-lactamase was assessed as a monitor of the ability of Bce44B to enhance the level of bacterial protein translocation. Overnight cultures of MM52-Bce44B, MM52-Oee1-Dhfr, MC4100-BceB and MC4100-Oee1-Dhfr cells were used as inocula in parallel experiments. One set of cultures was grown at 30° C. throughout the experiment and the other set was shifted from 30° C. to 37° C. Samples of cells were harvested at time points representing 0, 1 and 2 hours postshift. Whole cell proteins were subjected to SDS-PAGE and immunoblotting with anti-β-lactamase IgGs. The number of cells assessed was adjusted and normalized before loading the gels. Both MC4100-based strains (MC4100-Bce44B and MC4100-Oee1-Dhfr) showed predominantly the mature form and precursor forms of β-lactamase at both permissive and non-permissive temperatures and at all time points. The MM52-Oee1-Dhfr cells displayed protein translocation deficiencies at both permissive and non-permissive temperatures which were manifested as high ratios of precursor to mature forms of β-lactamase such as that observed in MM52 cells carying only the vector plasmid. In contrast, the Bce44B-expressing MM52 strain behaved in the same way as the wild-type counterpart, displaying predominantly the transported mature form of β-lactamase at both permissive and non-permissive temperatures.

Sensitivity to sodium azide was employed to furter demonstrate the effects of the Bce44B complementation on protein translocation in the MM52 strain. Overnight cultures of MM52-Bce44B, MM52-Oee1-Dhfr, MC4100-Bce44B, and MC4100-Oee1-Dhfr cells were used as inocula for parallel experiments. These freshly inoculated cultures were grown at 30° C. for two hours in media containing increasing concentrations of sodium azide (from 0 to 1 MM). Cells were then harvested, and normalized according to cell number before analysis. The immunoblot results showed that MM52-Oee1-Dhfr-expressing cells displayed protein translocation deficiencies. The precursor form of P4actamase began appearing at a very low azide concentration (0.125 mM), while MM52-Bce44B-containing cells demonstrated the same behavior as the wild-type counterparts, e.g., MC4100-Bce44B or MC4100-Oee1-Dhfr-expressing cells, where precursor forms of β-lactamase were not detected until the sodium azide concentration reached 0.25–0.375 mM. Azide sensitivity characteristics were firther assessed by growing both wild-type and mutant bacterial lines in the media containing 0.5 mM sodium azide for 0, 1 and 2 hr. The immunoblot results showed the same characteristics as in the above experiments, namely that the presence of Bce44B resulted in the same profile of β-lactamase transport as the wild-type cells despite the secA mutation.

The complementation results collectively indicate that β-lactamase transport in the secA mutant is influenced by Bce44B directly in enhancing transport rather than by upregulation of the bacterial protein translocation machinery.

Analysis of protein translocation using deletion constructs of Bce44B:

Two deletion mutants of Bce44B were made by removing the N-terminal 42 amino acids and by removing 17 amino acids at the carboxyl end of the N-terminal 42 amino acid region. These are designated K117 (FIG. 4) and K118 (FIG. 5), respectively. The two deletion constructs of Bce44B were subjected to the same set of analyses as outlined above to assess the effects of the deletions on the protein translocation enhancement property of Bce44B.

The deletion constructs were introduced into JM109 (DE3) as described in Example 7, using the same T7 promoter-bearing plasmid vector to facilitate expression. The immunoblotting results indicate that both deletions affected the expression level of Bce44B in E. coli. The lowest levels were exhibited by cells harboring K118. Cells harboring K117 also demonstrated lower levels compared to unaltered Bce44B-containing cells but substantially higher levels than K118. The level of mature β-lactamase in K117-harboring cells was lower than unaltered Bce44B-containing cells on a per cell basis. The β-lactamase levels were the lowest in the K118-containing cells. The lower level of translocated β-lactamase was reflected in the level of ampicillin concentration tolerated by the corresponding strain. In contrast to the Bce44B-containing cells, K117 and K118 exhibit differences in the ability to form colonies on plates with increasing concentrations of ampicillin. K117 can only form colonies at 500 µg/ml ampicillin and K118 can only form colonies up to 250 µg/ml ampicillin.

Wild-type Bce44B is targeted to both outer and inner membranes. The amount of Bce44B present in the outer membrane is higher than in the inner membrane. In comparison to Bce44B, K117 is still targeted to both inner and outer membranes despite the deletion. Distribution of the truncated K117 protein occurred in the same fashion as for the wild-type Bce44B protein, albeit at significantly lower amounts. The K118 deletion protein is targeted only to the inner membrane in even lower amounts than either Bce44B or K117. Both K117 and K118 displayed resistance to thermolysin to the same degree as unaltered Bce44B and were completely sensitive only in the presence of 0.1% Triton X-100. In conclusion, the two deletions represented by K117 and K118 appear to affect the function of Bce44B in protein translocation.

Azide sensitivity experiments were conducted on the K117- and K118-containing cells and compared to Bce44B- and Oee1-Dhfr-expressing cells using liquid cultures containing increasing concentrations of sodium azide (0 mM, 0.125 mM, 0.25 mM, 0.375 mM, 0.5 mM, 0.625 mM, 0.75 mM, 0.875 mM, 1 mM) for two hours. The results show increasing amounts of the precursor form with a concomnitant decrease in the amount of the mature form of β-lactamase in all four types of cells. The azide inhibition of protein translocation patterns for K117 and K118 was similar to the inhibition pattern for Oee1-Dhfr-containing cells.

The results collectively suggest that the deletions affected the protein transport enhancing ability of Bce44B protein. These Bce44B mutants are good candidates for use in a dominant-negative approach to reduce the activity of a naturally-occurring Bce44B protein.

Technological applications:

Bce44B is a member of the Com44/Cim44 chloroplast envelope proteins. This invention provides, for the first time, evidence that Bce44B is part of the chloroplast protein import apparatus and can transport substances across plant membranes. One surprising and important advantage of Bce44B protein is its unique capacity to effectively transport substances by itself without requiring a multicomponent transport assembly which would be difficult to incorporate successfully into other organisms. As evidence of this advantage, data is provided demonstrating that Bce44B can translocate substances across bacterial (prokaryotic) membranes as well as plastid membranes. Both systems recognize and incorporate Bce44B in the same manner relative to the direction of protein translocation.

As in the chloroplast envelope, translocating precursor proteins are found in close physical proximity to Bce44B in the bacterial membrane. The integrated protein in the bacterial membrane additionally affects the SecA-dependent protein export of alkaline phosphatase and β-lactarnase by enhancing their levels via a less azide-sensitive mode of action. It is not known if Bce44B acts independently by forming new more azide-tolerant pathways, most likely via the assembly of chimeric protein translocation machinery, or by altering a portion of the pathways already in existence, thus becoming less azide-sensitive overall (similar to the systems found in chloroplasts). The combination of the chemical cross-linking results and the partial nature of the azide insensitivity tends to point to the first possibility.

This invention also provides evidence of parallelism of protein translocation in bacteria and plastids, demonstrating that there are common features in protein translocation systems among different organisms and providing, as a result, methods of translocating substances for any organism. Thus, the methods of this invention provide a novel and powerful way to elucidate the roles and functions of components of the plastid protein transport machinery by utilizing bacteria, and to further allow access to and application of all of the molecular tools available for studying various aspects of bacteria for studies of plastid protein import.

Since the mitochondrion is thought to have evolved in a similar fashion to plastids via an endosymbiotic mode, the bacterial approach described for studying protein uptake into plastids can also be utilized for constructing methods to alter import of substances in mitochondria. The mode of protein importation in mitochondria and the structure of the organelle closely resemble those found in plastids; thus, those of skill in the art will recognize that minor modification is required to apply the methods described in this invention for use in mitochondria and other double membrane compartments.

In another aspect, this invention relates to antibodies which bind the polypeptides described herein. Such antibodies can be used to locate sites of translocation or membrane integration activity in cells. Fusion proteins comprising Bce44B and an additional peptide, such as a protein tag, can also be used to detect sites of Bce44B activity in cells of prokaryotes and eukaryotes. Detection of sites of activity is useful to help understand the structure and function of membranes, especially those of plastids and mitochondria. These antibodies can also be useful to inhibit translocation of substances across membranes or integration of substances into membranes.

Isolated DNA is introduced into plant cells of a target plant by well-known methods, such as Agrobacterium-mediated transformation, microprojectile bombardment, microinjection or electroporation. Cells carrying the introduced isolated and/or recombinant DNA can be used to regenerate transgenic plants which have altered phenotypes, therefore becoming sources of additional plants either through seed production or non-seed asexual reproductive means.

The methods of this invention can be used to provide plants, seeds, plant tissue culture, plant parts, cells, and protoplasts containing one or more nucleic acids which comprise a modified or isolated introduced gene encoding a Bce44B protein or its functional equivalent which alters transport across a cellular membrane or incorporation of molecules into membranes. Plants parts can include roots, leaves, stems, flowers, fruits, meristems, epicotyls, hypocotyls, cotyledons, pollen and embryos.

The present invention also relates to transgenic plants, or cells or tissues derived from such plants, in which membrane transport or incorporation of molecules into membranes is altered directly or indirectly through application of the methods of this invention. The term "transgenic plants" includes plants or photosynthetic protists which contain introduced DNA which, if transcribed and translated, changes the amount or type of one or more plant products compared to a wildtype (naturally-occurring) plant of the same species or variety grown under the same conditions. Transgenic plants include those into which isolated and/or recombinant nucleic acids have been stably inserted and their descendants, produced from seed, vegetative propagation, cell, tissue or protoplast culture, or the like wherein such alteration is maintained. The introduced DNA which is originally inserted into the plants or plant cells or protoplasts can include additional copies of genes found in the naturally-occurring organism.

In one embodiment, the methods of this invention can be used to stably transform the genome of plastids or mitochondria. Whether through nuclear, plastid, or mitochondrial constructs, the ability to alter plastid or mitochondrial components is a great advantage. Especially in plants, the alteration can be contained because the plastids of most plants are maternally inherited, thus the altered genes will not be transmitted in the pollen which is freely disseminated. The risk of transmission to wild-type (native) plants is then greatly reduced. Further, disruption of mitochondria, especially in pollen or pollen tube formation can be desirable for transgenic containment when the disruptive peptides or polypeptides are expressed in a tissue-specific manner and/or during a particular stage of development. Methods of producing pistil-specific or anther-specific expression of a nucleotide sequence to produce either female or male sterility, respectively, can be found, for example, in Nasrallah et al. (1994) PCT/US94/04557 (WO 94/25613).

Those of skill in the art will recognize the methods of this invention for enhancing import or export of naturally-occurring plant products such as proteins, oils, carbohydrates, and combinations thereof into and out of organelles or into or out of cells has the possibility of an almost infinite number of applications. Besides enhancing accumulation or export of naturally-occuting products, the transgenic plants can also contain introduced genes which encode useful products whose accumulation or harvest is facilitated by enhanced membrane transport. In particular, antigens for vaccine purposes, antibodies, blood products, enzymes and the like, as well as insect or disease inhibitors for plants are examples of products which can be provided from other sources including mammals.

For example, transgenic plants expressing foreign peptides, such as the binding subunit of E. coli heat-labile enterotoxin have been shown to accumulate these antigens in leaves and tubers (Haq et al. (1995) *Science* 268:714–716). Further, transgenic plant cells have been shown to express and assemble secretory antibodies (Ma et al. (1995) *Science* 268:716). Enhanced membrane transport as described in the present invention can be used to increase the solubilization and accumulation of such plant-derived products in the edible portions of plants or in the portions of plants intended to be harvested for extraction of these compounds, or even to change the size of plant parts. Transport can be altered, for example, in any plant organ; i.e., stems, roots, leaves, flowers and fruits.

The methods provided herein can enhance the accumulation and/or transport of substances for plant disease resistance. For example, fungal pathogens (e.g., Sclerotinia sp.) produce oxalic acid which helps to break down the cell walls of plants and promotes fingal growth. Isolated DNA encoding oxalate decarboxylase or oxalate oxidase can be inserted into plants wherein the expressed enzyme can be solubilized by Bce44B protein and its accumulation can be directed through Bce44B-assisted transport to cell walls and intercellular spaces where it can degrade and detoxify oxalic acid, thereby protecting plants against this pathogen. See, for example, European Patent Applications EP 673,416 (Sep. 27, 1995) and EP 531,498 (Mar. 17, 1993). These enzymes can also be used to reduce the oxalic acid content of plants in which the oxalic acid content is high and results in toxicity of the plant or plant part when ingested (e.g., rhubarb).

Those of skill in the art can understand that the variety of transgenic products which can be produced and translocated in prokaryotic and eukaryotic organisms by the methods described herein is broad and encompasses many important naturally-occurring and foreign substances which are regulatory or are products themselves. These include, for example, storage products such as sugars, starches, pigments, and the like. If naturally-occurring in the photosynthetic organism, the product may be produced at higher levels, compartmentalized in a different part of the cell, such as the plastid, mitochondrion, or vacuole, or even in a different organ, such as the flower, seed, root or leaf. Thus, pigments can be expressed and/or accumulated at higher levels to enhance the color of the plant or plant part normally producing the pigment by methods provided herein. Further, through the same methods, a novel color can be produced in a plant or imparted to a plant organ by linking the gene encoding the pigment (or the proteins which catalyze pigment synthesis) to the constructs described herein so that the pigment gene products are expressed and translocated.

Alternatively, this invention provides methods for varying the phenotype of seeds and other storage organs of plants. These novel products or combination of products can be provided by enhancing the translocation of molecules to be stored or by modifying the composition of cellular membranes to alter the translocation of particular products. Thus, in addition to increasing the overall amount of stored substances, thus increasing the nutritive value of the seed, alterations can include modifying the fatty acid composition in seeds by changing the ratio and/or amounts of the various fatty acids as they are produced. Alternatively, improvements in the amino acid composition of storage proteins can be generated. Of particular interest as target substances are the storage proteins of seeds, such as napin, cruciferin, β-conglycinin, phaseolin, brazil nut protein, other 2S or 7S proteins, or the like, as well as proteins involved in fatty acid biosynthesis, such as acyl carrier protein.

When useful proteins are expressed at high levels in the transgenic plants (or other eukaryotes of this invention), these levels could be toxic to the cell or organism. Therefore, it can be important to sequester such highly expressed proteins in compartments such as plastids, especially plastids of storage tissues. As an example, genetically-engineered plants which express Bt (*B. thuringiensis*) toxins as recombinant proteins may show inhibited growth due to high levels of the expressed toxins, which are intended to provide insect resistance by poisoning grazing insects. However, increased levels of these proteins will be required as endemic populations of insects develop resistance to the presently expressed levels in recombinant plant tissues. Sequestering this protein in the plastids following expression either within or outside of the plastid, could reduce its toxic effects in the cell. Vacuoles can also be used to sequester toxic compounds.

Enhanced expression and translocation of substances into plastid compartments or other organelles can facilitate a preferred or more efficient method of purifying or processing protein products or other products generated from a transgenic plant. Further, enhancing translocation of a transgenic product into plastids can provide a separate environment in which high concentrations of proteins can induce an "inclusion bodies" effect similar to that commonly observed in bacterial overexpression, thus facilitating isolation of the preferred product.

To produce transgenic plants of this invention, a construct comprising the gene for Bce44B or nucleic acid encoding its functional equivalent and a promoter are incorporated into a vector as described in Example 19 or through other methods known and used by those of skill in the art. The construct can also include any other necessary regulators such as terminators or the like, operably linked to the coding sequence. It can also be beneficial to include a 5' leader sequence, such as the untranslated leader from the coat protein mRNA of alfalfa mosaic virus (Jobling, S. A. and Gehrke, L. (1987) *Nature* 325:622–625) or the maize chlorotic mottle virus (MCMV) leader (Lommel, S. A. et al. (1991) *Virology* 81:382–385). Those of skill in the art will recognize the applicability of other leader sequences for various purposes.

Targeting sequences are also useful and can be incorporated into the constructs of this invention. A targeting sequence is usually translated into a peptide which directs the polypeptide product of the coding nucleic acid sequence to a desired location within the cell, such as to the plastid, and becomes separated from the peptide after transit of the peptide is complete or concurrently with transit. Examples of targeting sequences useful in this invention include, but are not limited to, the yeast mitochondrial presequence (Schmitz et al. (1989) *Plant Cell* 1:783–791), the targeting sequence from the pathogenesis-related gene (PR-1) of tobacco (Cornellisen et al. (1986) *EMBO J*. 5:37–40), vacuole targeting signals (Chrispeels, M. J. and Raikhel, N. V. (1992) *Cell* 68:613–616), secretory pathway sequences such as those of the ER or Golgi (Chrispeels, M. J. (1991) *Ann. Rev. Plant Physiol. Plant Mol. Biol*. 42:21–53). Intraorganellar sequences may also be useful for internal sites, e.g., thylakoids in chloroplasts. Theg, S. M. and Scott, S. V. (1993) *Trends in Cell Biol*. 3:186–190.

In addition to 5' leader sequences, terminator sequences are usually incorporated into the construct. In plant constructs, a 3' untranslated region (3' UTR) is generally part of the expression plasmid and contains a polyA termination sequence. The termination region which is employed will generally be one of convenience, since termination regions appear to be relatively interchangeable. The octopine synthase and nopaline synthase termination regions, derived from the Ti-plasmid of *A. tumefaciens*, are suitable for such use in the constructs of this invention.

Any suitable technique can be used to introduce the nucleic acids and constructs of this invention to produce transgenic plants with an altered genome. For grasses such as maize, microprojectile bombardment (see for example, Sanford, J. C. et al., U.S. Pat. No. 5,100,792 (1992) can be used. In this embodiment, a nucleotide construct or a vector containing the construct is coated onto small particles which are then introduced into the targeted tissue (cells) via high velocity ballistic penetration. The vector can be any vector which permits the expression of the exogenous DNA in plant cells into which the vector is introduced. The transformed cells are then cultivated under conditions appropriate for the regeneration of plants, resulting in production of transgenic plants. Transgenic plants carrying the construct are examined for the desired phenotype using a variety of methods including but not limited to an appropriate phenotypic marker, such as antibiotic resistance or herbicide resistance, or visual observation of the time of floral induction compared to naturally-occurring plants.

Other known methods of inserting nucleic acid constructs into plants include Agrobacterium-mediated transformation (see for example Smith, R. H. et al., U.S. Pat. No. 5,164,310 (1992)), electroporation (see for example, Calvin, N., U.S. Pat. No. 5,098,843 (1992)), introduction using laser beams (see for example, Kasuya, T. et al., U.S. Pat. No. 5,013,660 (1991)) or introduction using agents such as polyethylene glycol (see for example Golds, T. et al. (1993) Biotechnology, 11:95–97), and the like. In general, plant cells may be transformed with a variety of vectors, such as viral, episomal vectors, Ti plasmid vectors and the like, in accordance with well known procedures. The method of introduction of the nucleic acid into the plant cell is not critical to this invention.

The methods of this invention can be used with in planta or seed transformation techniques which do not require culture or regeneration. Examples of these techniques are described in Bechtold, N. et al. (1993) *CR Acad. Sci. Paris/Life Sciences* 316:118–93; Chang, S. S. et al. (1990) *Abstracts of the Fourth International Conference on Arabidopsis Research*, Vienna, p. 28; Feldmann, K. A. and Marks, D. M (1987) *Mol. Gen. Genet.* 208:1–9; Ledoux, L. et al. (1985) *Arabidopsis Inf. Serv.* 22:1–11; Feldmann, K. A. (1992) In: Methods in Arabidopsis Research Ads. Koncz, C., Chua, N-H, Schell, J.) pp. 274–289; Chee et al., U.S. Pat. Ser. No. 5,376,543.

The transcriptional initiation region may provide for constitutive expression or regulated expression. Many promoters are available which are functional in plants. The term "promoter" refers to a sequence of DNA, usually upstream (5') of the coding region of a structural gene, which controls the expression of the coding region by providing recognition and binding sites for RNA polymerase and other factors which may be required for initiation of transcription.

Constitutive promoters for plant gene expression include, but are not limited to, the octopine synthase, nopaline synthase, or mannopine synthase promoters from Agrobacterium, the cauliflower mosaic virus (35S) promoter, the figwort mosaic virus (FMV) promoter, and the tobacco mosaic virus (TMV) promoter. Constitutive gene expression in plants can also be provided by the glutamine synthase promoter (Edwards et al. (1990) *PNAS* 87:3459–3463), the maize sucrose synthetase 1 promoter (Yang et al. (1990) *PNAS* 87:4144–4148), the promoter from the Rol-C gene of the TLDNA of Ri plasmid (Sagaya et al. (1989) *Plant Cell Physiol*. 30:649–654), and the phloem-specific region of the pRVC-S-3A promoter (Aoyagi et al. (1988) *Mol. Gen. Genet*. 213:179–185).

Heat-shock promoters, the ribulose-1,6-bisphosphate (UBP) carboxylase small subunit (ssu) promoter, tissue specific promoters, and the like can be used for regulated expression of plant genes. Developmentally-regulated, stress-induced, wound-induced or pathogen-induced promoters are also useful.

The regulatory region may be responsive to a physical stimulus, such as light, as with the RUBP carboxylase ssu promoter, differentiation signals, or metabolites. The time and level of expression of the sense or antisense orientation can have a definite effect on the phenotype produced. Therefore, the promoters chosen, coupled with the orientation of the exogenous DNA, and site of integration of a vector in the genome, will determine the effect of the introduced gene.

Specific examples of regulated promoters also include, but are not limited to, the low temperature Kin1 and cor6.6 promoters (Wang et al. (1995) *Plant Mol. Biol.* 28:605; Wang et al. (1995) *Plant Mol. Biol.* 28:619–634), the ABA inducible promoter (Marcotte Jr. et al. (1989) *Plant Cell* 1:969–976), heat shock promoters, such as the inducible hsp70 heat shock promoter of *Drosphilia melanogaster* (Freeling, M. et al. (1985) *Ann. Rev. of Genetics* 19: 297–323), the cold inducible promoter from *B. napus* (White, T. C. et al. (1994) *Plant Pysiol*. 106:917), the alcohol dehydrogenase promoter which is induced by ethanol (Nagao, R. T. et al., Miflin, B. J., Ed. *Oxford Surveys of Plant Molecular and Cell Biology*, Vol. 3, p 384–438, Oxford University Press, Oxford 1986), the phloem-specific sucrose synthase ASUS 1 promoter from Arabidopsis (Martin et al. (1993) *Plant J.* 4:367–377), the ACS1 promoter (Rodrigues-Pousada et al. (1993) *Plant Cell* 5:897–911), the 22 kDa zein protein promoter from maize (Unger et al. (1993) *Plant Cell* 5:831–841), the ps1 lectin promoter of pea (de Pater et al. (1993) *Plant Cell* 5:877–886), the phas promoter from *Phaseolus vulgaris* (Frisch et al. (1995) *Plant J.* 7:503–512), the lea promoter (Thomas, T. L. (1993) *Plant Cell* 5:1401–1410), the E8 gene promoter from tomato (Cordes et al. (1989) *Plant Cell* 1:1025–1034), the PCNA promoter (Kosugi et al. (1995) *Plant J.* 7:877–886), the NTP303 promoter (Weterings et al. (1995) *Plant J.* 8:55–63), the OSEM promoter (Hattori et al. (1995) *Plant J.* 7:913–925), the ADP GP promoter from potato (Muller-Rober et al. (1994) *Plant Cell* 6:601–604), the Myb promoter from barley (Wissenbach et al. (1993) *Plant J.* 4:411–422), and the plastocyanin promoter from Arabidopsis (Vorst et al. (1993) *Plant J.* 4:933–945).

Transgenic plants of this invention can contain isolated or recombinant nucleic acids which preferentially modify plastid transport pathways which are present in green tissues, or which are present in actively growing tissues or in storage tissues or organs such as seeds. The plastids of plant tissues are desirable targets for modifications to provide increased photosynthetic capacity or to provide mechanisms for disease or stress resistance. Alternatively, transgenic plants can contain introduced isolated or recombinant nucleic acids which alter the transport capability of other organelles or of the plasma membrane of cells. In this manner, different products can be accumulated, exported or imported to modify the capability of the plant to express and localize one or more products compared to the expression and accumulation of the same product(s) in a plant of the same variety without said introduced isolated or recombinant nucleic acids when grown under identical conditions.

Further, this invention includes a method of producing a transgenic plant containing, in addition to isolated nucleic acids which encode a Bce44B polypeptide or its functional equivalent so that membrane transport is altered, at least one nucleic acid which encodes a polypeptide for production of a useful foreign product. Coupled with the altered membrane transport system in the cells of the plant, it is possible to design a plant wherein, when all of the inserted nucleic acids are expressed, the result is the large scale and inexpensive production of valuable proteins or other products in a particular plant tissue or at a particular stage of development.

The methods described herein can be applied to all types of plants and other photosynthetic organisms, including: angiosperms (monocots and dicots), gymnosperms, spore-bearing or vegetatively-reproducing plants and the algae (including the blue-green algae). Further, the methods of this invention are suited to enhance translocation of substances in all prokaryotes. It is understood that prokaryotic organisms lack plastids and other organelles, but that the photosynthetic membranes or cell membranes of these organisms can be modified to alter photosynthetic capacity and products and/or translocation of other products through expression of a Bce44B polypeptide or its functional equivalent and incorporation of the same in the appropriate cellular membrane. It is also likely that the methods described herein can be applied, without undue experimentation, to enhance transport of substances in nonphotosynthetic eukaryotes such as the fungi and Animalia, particularly in mitochondria, due to their analogous evolutionary history with plastids.

Transgenic plants containing the constructs described herein can be regenerated from transformed or transfected cells, tissues or portions of plants by methods known to those of skill in the art. A portion of a plant is meant to include any part capable of producing a regenerated plant. Thus, this invention encompasses a cell or cells, tissue (especially meristematic and/or embryonic tissue), protoplasts, epicotyls, hypocotyls, cotyledons, cotyledonary nodes, pollen, ovules, stems, roots, leaves, and the like. Plants may also be regenerated from explants. Methods will vary according to the plant species.

Seed can be obtained from the regenerated plant or from a cross between the regenerated plant and a suitable plant of the same species. Alternatively, the plant may be vegetatively propagated by culturing plant parts under conditions suitable for the regeneration of such plant parts. For example, plants can be regenerated from cultured pollen, protoplasts, meristems, hypotcotyls, epicotyls, stems, leaves, and the like.

Isolated and purified Bce44B protein or polypeptides, and epitopic fragments thereof, can also be used to prepare antibodies which can be used, for example, for localization of sites of Bce44B function and to analyze developmental pathways in plants. Antibodies that specifically bind a Bce44B protein can detect Bce44B expression in specific cells or tissues of plants. This information can be used to determine how and when Bce44B acts to transport substances across membranes.

Antibodies used in the methods of the invention can be polyclonal, monoclonal, or antibody fragments, and the term antibody is intended to encompass polyclonal antibodies, monoclonal antibodies and antibody fragments. Antibodies of this invention can be raised against isolated or recombinant Bce44B proteins or polypeptides. (See, e.g., Examples 21–23). Preparation of immunizing antigen, and antibody production can be performed using any suitable technique. A variety of methods have been described (see e.g., Harlow, E. and D. Lane (1988) *Antibodies: A Laboratory Manual*, Cold Spring Harbor Laboratory Press, Cold Spring Harbor, N.Y.; Ausubel et al. (1994) *Current Protocols in Molecular Biology*, Vol. 2, Chapter 11 (Suppl. 27) John Wiley & Sons: New York, N.Y.).

Antibodies used in the methods of this invention can be labeled or a second antibody that binds to the first antibody can be labeled by some physical or chemical means. The label can be an enzyme which is assayed by the addition of a substrate which upon reaction releases an ultraviolet or visible light-absorbing product or it can be a radioactive substance, a chromophore, or a fluorochrome. E. Harlow and D. Lane (1988) supra.

The Bce44B protein component works closely with the 97 kDa component of the plastid protein import machinery. The stoichiometry of Bce44B relative to other components of the plastid protein transport machinery, such as the 97 kDa (Cim97) component, appears to be a key operating factor in the import mechanism. Stoichiometry differences can provide a method to detect changes in import activity in plant tissues. Differences in stoichiometry, such as a higher ratio of Bce44B to Cim97, can be used, for example, to detect plants that will give rise to greater biomass and larger seeds. Larger seeds correlate with alterations to the stoichiometry of the components of plastid protein import machinery in naturally occurring plants and even between different cultivars. These values can be detected by the antibodies disclosed herein. This approach can also be developed into a diagnostic kit which can be used to determine whether a plant will yield, for example, larger seeds. A diagnostic kit for this purpose can be valuable tool by which plant breeders can screen for desirable products of breeding programs before maturation. There are many advantages of having an early measurement from such a kit. Most important, it would eliminate the laborious task of dealing with all products of breeding and allow an early focus on the most promising plants in a population.

The observed differences in stoichiometry of Bce44B relative to other components of the plastid protein transport machinery also suggest that the action of Bce44B can be regulated or affected by the introduction of other components of the plastid protein transport machinery, e.g., Cim97. Thus, it is possible to alter or fine tune the activity of the Bce44B gene by introducing regulators to the DNA constructs of this invention. Selected effects in the resulting tansgenic plants can be achieved by manipulation of the components to a relationship that provides the desired plant traits, e.g., seed size.

In another method of this invention, Bce44B polypeptide or its functional equivalent can be used to detect and analyze protein/protein transport interactions. Fusion proteins for this purpose can be prepared by fusing Bce44B nucleic acid encoding a Bce44B polypeptide or its fimctional equivalent with heterologous DNA encoding a different polypeptide (one not related or homologous to the Bce44B polypeptide), such as a protein tag. The resulting fusion protein can be prepared in a prokaryotic cell (e.g., *E. coli*), isolated, labeled and used essentially like antibodies to detect binding sites of Bce44B/protein interactions. See Ron and Dressler (1992) *Biotech* 13:866–869; Smith and Johnson (1988) *Gene* 67:31–40.

Those skilled in the art can recognize the advantages of using selective promoters as well as constitutive promoters in the plasmids and vectors of this invention. Selective promoters can be used to alter the transport of substances during times of stress or at particular growth stages. For example, increased photosynthesis through increased import of precursor materials such as chlorophyll binding proteins into the plastid can boost the growth of a seedling so that it is well established and larger than a naturally-occurring plant when periods of stress occur. Thus, it can have a deeper, more extensive root system which gives it more access to water and helps it survive droughts.

Larger seeds produced by transgenic plants can result in more product and better germination. These seeds can also be planted deeper since the increased reserve metabolites will allow them to grow more quickly (or over a longer period of time), if necessary, before the seedling reaches the surface of the soil. Increased transport can result in larger roots (e.g., carrots) or in larger tubers (e.g., potatos).

Enhanced protein transport through incorporation of the Bce44B gene can increase the overall vegetative size of plants, thus increasing yields. This growth enhancement is probably due to the plant's need to regulate internal stress relating to protein concentration and to the osmotic preference of cellular compartments such as the plastid, mitochondrion or vacuole. Manipulation of protein concentration through alteration of protein transport may disturb osmotic pressures in such compartments. For example, to compensate for higher osmotic pressure in a plastid (due to increased protein import into the plastid), the cell could signal division of the plasid. If this division were not adequate to restore normal pressure, cell division could result. Eventually, these effects would produce faster growth and larger plants. In accordance with this model, incorporation and expression of the Bce44B gene in plants is a method of eliciting faster growth and producing larger plants.

Further, antisense or dominant-negative constructs can be used to inhibit transport of substances, thereby accumulating substances at selected sites. Since Bce44B is a general component of a plant system, site-specific or inducible promoters can be used to prevent lethal effects due to complete inhibition.

In another aspect, the methods of this invention can provide means for the selection of cells and organisms which have been infected, transfected or transformed. Through these means, selectable markers are available without concern for the toxicity of the products, their effect on the environment, or concern that they will have to be regulated. At present, selection methods for plants, plant cells or tissues which have successfully incorporated inserted nucleic acid constructs usually involve detection of gene products of marker genes inserted as part of the nucleic acid construct. The most common strategy for obtaining transgenic cells has been the inclusion of drug-resistance determinants, such as kanamycin resistance, in the vector inserted into the cells. Although addition of drugs to growth medium allows selection for cells containing the incorporated nucleic acids, addition of antibiotics is unacceptable in many instances because of cost and possible contamination of the end product.

Inclusion of additional Bce44B protein into plastids results in enhanced transport of materials into plastids. This in turn leads to increased photosynthetic end products such as carbohydrates and lipids which are stored in seeds. The seeds of such transgenic plants are larger than the wildtype variety (see Example 20) thereby providing a marker which can be used reliably to circumvent the inclusion of antibiotics to the culture medium. Therefore, a method of detecting transformation, infection or transfection in a cell comprises: incorporating isolated nucleic acid encoding Bce44B or its functional equivalent into the cell; maintaining the cell or organism under conditions appropriate for expression of Bce44B or its functional equivalent; and then detecting the enhanced transport in the cell, wherein detection of enhanced transport is indicative of a transformed, infected or transfected cell. Using this method, a plant derived from a transformed, infected or transfected cell produces an enlarged seed compared to a seed of an untransformed, infected, or transfected plant of the same variety under the same growing conditions, and the enlarged seed provides a selectable marker.

In one particular embodiment, the constructs of this invention can be used as a selectable marker and means of removing undesirable insertions of Ti plasmid DNA to avoid potential regulatory problems with transgenic plants and plant products. During Agrobacterium-mediated transformation, part of the Ti plasmid is incorporated in the plant genome. The DNA encoding Bce44B can be incorporated into another part of a typical Agrobacterium binary vector, outside the T-DNA region, and placed under the control of an appropriate promoter for expression in plants to allow detection of transformation. Thus, the Ti plasmid portion is "tagged" with this gene, thereby producing a visual marker which segregates with the Ti plasmid portion. Detection of transformation can be determined by examining protein import modifications or visually by examining transgenic seed size and other phenotypic characteristics of increased transport. The Ti plasmid can then be selected out through subsequent generations by appearance of increased transport (i.e., larger plants, etc.) or by larger seeds resulting from expression of the Bce44B DNA. Normally-sized seeds would indicate the loss of the Bce44B-linked Ti plasmid but presumably still contain the transgene of choice. Other undesirable genes can be expunged by this method. The resulting transgenic plants can then be transformed again via the same approach for many cycles. Each cycle will result in the addition of a new transgene but remove the Bce44B marker gene and the accompanying Ti plasmid DNA sequence. Thus, this method permits the re-use of the selectable marker "Bce44B" within one or two generations, which is currently difficult to achieve for multigenic manipulations.

Likewise, increased photosynthetic capability leads to faster growth of cells, tissue culture, and the individual plants compared to wildtype materials, thus providing other means to identify successful incorporation of transport protein nucleic acids. Thus, increased transport can potentially bypass culturing as commonly practised.

Increased foreign product can also constitute a marker which allows for selection of cells or organisms having incorporated nucleic acids encoding both the Bce44B protein or its functional equivalent and one or more foreign products. Peptides, phosphatases, insulin, antibodies, or even livestock hormones can be used as such markers. For example, a bacterial cell producing human growth hormone (hGH) will show an increase in translocation of hGH if Bce44B or an equivalent polypeptide is incorporated into the bacterial cell membranes. Such substances can be detected by immunodetection, enzymatic assay or the like.

Thus, one method of detecting transformation, infection or transfection in a cell comprises; incorporating both isolated nucleic acid encoding Bce44B or its functional equivalent and another gene encoding a product into a cell or organism; maintaining the cell or organism under conditions appropriate for expression of Bce44B or its functional equivalent and the product encoded by the other gene; and then detecting the enhanced transport of the product or an endogenous polypeptide, wherein detection of enhanced transport is indicative of a transformed, infected or transfected cell.

Increased resistance to ampicillin or increased ability to grow under conditions of phosphate starvation provide methods by which transgenic cells carrying Bce44B and an additional gene for a product can be selected from untransformed cells. For example, compounds such as alkaline phosphatase can provide the basis for a complementation system for the selection and maintenance of such product genes in bacterial or yeast hosts. Genes encoding Bce44B protein (or its functional equivalent), and a commercially-important product can be incorporated into plasmids and the plasmids inserted into host cells which are maintained in environments requiring additional translocation of alkaline phosphatase by the cells. Through complementation of transport genes of the host, which defect cannot be overcome without additional translocation of alkaline phosphatase or nutritional supplementation, the plasmids are stabilized in the host cells. Thus, plasmids carrying genes for commercially-important products can be maintained in the cells with the increased translocation of alkaline phosphatase providing the stabilization of the product-producing cells. A similar strategy is possible in plants and would most likely involve complementation of plastid or mitochondrial genes.

Those of skill in the art will recognize the advantages of being able to alter translocation processes in bacteria, such as the secretion or import of substances, and even to influence expression and solubilization of products produced in these prokaryotic cells. The method of increasing translocation of fermentation products for harvesting through the activity of Bce44B or its functional equivalent is an extremely valuable and useful mechanism by itself.

There are an unlimited number of products which either isolated from or harvested as part of the organism producing them would be useful. In addition, strains of bacteria harboring genes encoding proteins which enhance translocation (and therefore, utilization) of substances can be used to innoculate the intestines of cows and other ruminants which depend on microbes for their digestive processes.

Bacterial cells can easily be grown to high densities, which is the basis for the inexpensive, high-yielding fermentation processes developed for the production of protein products on a large industrial scale. However, the production and transport of foreign proteins in bacteria do not always reach optimal and economically viable levels, especially when fusion proteins are overproduced. The levels expressed and translocated depend largely on the fusion protein in question and the bacterium's ability to efficiently recognize, transport and process the particular foreign protein. Although translocation is achieved in principle by attaching an N-terminal signal peptide to the desired protein, the transported levels achieved relative to the levels of protein expressed are not proportionally high in most cases. The translocation of foreign proteins into the media or periplasm is desirable to reduce processing cost. Translocation which results in secretion or exportation enhances the purity of the desired overexpressed product by physically partitioning the expressed product from cytoplasmic proteins. Such translocation avoids cytoplasmic toxicity, attack by endogenous proteases and N-terminal methionine extension. Furthermore, the accumulation of products in a more oxidizing environment where disulphide bond formation may proceed is highly desirable, so that the protein may fold into a soluble, biologically active conformation (Hockney (1994) *TIBS* 12:456; Missiakas et al. (1993) *Proc. Natl. Acad. Sci. USA* 90:7084).

The *E. coli* translocation machinery does not always work efficiently with overexpressed proteins. Although there have been relatively successful approaches for optimizing protein translocation, each strategy has limitations and the positive enhancements appear restrictive for general application, i e., not every protein works. One strategy is to engineer the signal peptide to make the protein a better substrate for the transport machinery (Klein et al. (1992) *Protein Eng.* 5:511). Another approach is to elevate components of the endogenous transport apparatus and this has met with some success for two fusion proteins, OmpA-human interleukin-6 and human granulocyte-colony stimulating factor (Perez-Perez et al. (1994) *Biotechnology* 12:178). However, as the authors in this latter study point out, the levels are still well below 100 percent.

There are also other means of enhancing translocation of heterologous proteins in *E. coli* via strategies that alter the efficiency of protein synthesis. Translational level strength is critical to the secretion of heterologous proteins in these bacteria. Simmons, L. C. and Ynasura, D. G. (1996) *Nature Biotechnology* 14:629–634. Thus translational efficiency can be improved by manipulating 5' untranslated region sequences.

Another strategy can involve overproduction of signal peptidase I in *E. coli*, which will result in a higher level of efficiency of protein translocation and maturation of hybrid secretory proteins. Van Dijl, J. M. et al. (1991) *Mol. Gen. Genet.* 227:40–48.

There appears to be a limit to which protein translocation can be enhanced in bacteria with current approaches. Most, if not all of the approaches are aimed at elevating or manipulating endogenous bacterial proteins involved in the secretory process. The alteration of bacterial components usually poses a problem because the bacterium itself can monitor and adjust the engineered aberrations, e.g., the secA component. The adjustment or downregulation usually reduces the magnitude of the improvement or abolishes the effect altogether (Oliver (1993) *Mol. Micro.* 7:159; Oliver et al. (1990) *J. Bioenerg. Biomembr.* 22:311).

One approach to overcome this problem is to further enhance transport by elevating the efficiency of protein translocation and/or by creating additional pathways for translocation via the introduction and expression of a central component of the plant plastid protein import apparatus in bacteria.

In the plastid, Bce44B may operate through interaction with a plastid-specific transit signal. Combined use in a protein transport system (e.g., the bacterial transport system), of Bce44B with proteins containing a plastid-specific transit signal could enhance transport of these proteins via Bce44B due to preferential interaction of Bce44B with this transit signal. Accordingly, this would provide a preferred substrate protein for transport with Bce44B, and Bce44B would selectively transport such proteins over endogenous secreted proteins.

In one embodiment, the vectors of this invention can be introduced into suitable hosts where the gene encoding the desired product can be expressed and the product produced. Preferred vectors for this application are T7 promoter-based plasmids; however, almost any type of expression plasmid would work, including those which are T3 promoter-based, SP6 promoter-based, lac promoter-based, trp promoter-based, and even inducible promoter-based. The vector may be formed by methods well known to those skilled in the art to which the invention relates. Such methods are described in greater detail in various publications identified herein, but especially Sambrook et al. (1989) *Molecular Cloning: A Laboratory Manual*, Cold Spring Harbor Laboratory, Cold Spring Harbor, N.Y., the contents of which are hereby incorporated by reference into the present disclosure in order to provide complete information concerning the state of the art.

Suitable hosts for these methods include *E. coli*, Bacillus sp., yeasts, pseudomonads, and cyanobacteria. Gene expression technology in these hosts is described in *Methods in Enzymology*, Volume 185, Goeddel, D. V., ed. (1990).

The resulting host/vector systems can be employed to manufacture the foreign product. The host cells containing the vectors are grown under suitable conditions permitting production of the foreign product and its transport into the periplasm and/or growth medium for recovery. Expression or membrane incorporation can occur under a wide range of conditions suitable for the growth of most hosts. As shown in Example 17, Bce44B-facilitated transport is not inhibited by low temperatures and very likely performs within the normal temperature range of all organisms; thereby requiring no special environmental conditions for its activity.

There are many advantages to the methods of this invention which provide a supplementary transport Bce44B protein or its functional equivalent in the inner and outer plasma membrane of the host organism (single membrane of a yeast host). First, translocation levels of the desired product will increase, resulting in higher yields of harvested product. This can come about because the product is not retained inside the cell where it can either be degraded or cause reduced growth of the host or both. Further, it is common for overexpressed foreign proteins to become insoluble, making processing of active proteins difficult or even impossible. For instance, proteins often have to be denatured and slowly renatured from insoluble inclusion bodies. The Bce44B protein is soluble when expressed inside a host bacterium and, if it binds precursor proteins or if fused to a precursor protein, it could enhance solubility of foreign proteins expressed in bacteria. Finally, there is evidence that additional export of the product through the bacterial cellular membrane by means of the Bce44B protein may increase expression of the product inside the cell. That is, synthesis of the product is propelled by its removal from the intracellular pool. Thus, in addition to reducing the costs of harvesting the fermentation product, increased yields can result from application of the methods of this invention.

Bacteria and yeasts are important organisms used for the commercial production of molecular products. Examples of such products include amino acids, enzymes, nucleotides, hormones, vitamins, antibiotics, antibodies and the like. More specifically, acid phosphatases, human growth hormones (Chang C. et al. (1987) *Gene* 55:189–196), growth factors (Wong, E. Y. et al. (1988) *Gene* 68:193–203), human interleukins (Denefle, P. et al., *Gene* 85:499–510), epidermal growth factors (Morioka-Fujimoto, K. et al. (1991) *J. Biol. Chem.* 266:1728–1732) and bovine somatotropin (Klein, B. K. et al. (1992) *Protein Engin.* 5:511–517) have been described for such applications. More examples are listed at Wrotnowski, C., *Genetic Engineering News* 16(12):6 (Jun. 15, 1996). Those of skill in the art will recognize that the above examples are not limiting and illustrate only a few of the products, manufacture of which can be enhanced by the methods of this invention.

The following examples describe specific aspects of the invention to illustrate the invention and provide a description of the methods used to isolate and modify the Bce44B gene and to identify its function in organisms. The examples should not be construed as limiting the invention in any way.

All citations in this application to materials and methods are hereby incorporated by reference.

EXAMPLES

Example 1

Subfractionation of chloroplasts and purification of chloroplast envelopes

Intact chloroplasts were purified from pea seedlings, *Pisum sativum* (cv. Improved Laxton's), as described by Bartlett et al. (1982) *Methods in Chloroplast Molecular Biology*, (Edelman, M., Hallick, R. B. and Chua, N. H., eds.) pp. 1081–1091 Elsevier Biomedical Press, Amsterdam, or Cline et al. (1985) *J. Biol. Chem.* 260:3691. The growth conditions were identical to those described previously (Ko and Cashmore (1989) *EMBO J.* 8:3187). Pea seedlings from 200 grams of seeds were grown for 9–11 days in growth chambers set at 21° C. under fluorescent lighting with 16:8 h light:dark photoperiod. Pea seedlings were harvested and homogenized in cold grinding buffer (50 mM HEPES-KOH pH 7.6, 0.33 M sorbitol, 0.05% bovine serum albumin, 0.1% ascorbate, 1 mM magnesium chloride, 1 mM manganese chloride, 2 mM $Na_2EDTA$) for 2–3 brief blendings of 5–10 sec at a setting of 5–6 on the Polytron Homogenizer. Percentages for all solutions are wt/vol unless otherwise indicated. All steps were conducted on ice with chilled equipment and solutions (4° C.). The homogenate was then filtered through three layers of Miracloth and the crude chloroplasts collected by centrifugation at 2,800×g for 3 minutes at 4° C. The crude chloroplast pellet was resuspended in 4 ml of grinding buffer and layered onto a 10–80% Percoll gradient (50 mM HEPES-KOH pH 7.6, 0.33 M sorbitol, 0.05% bovine serum albumin, 0.1% ascorbate, 0.15% polyethylene glycol, 0.05% Ficoll, 0.02% glutathione, 1 mM magnesium chloride, 1 mM manganese chloride, 2 mM $Na_2EDTA$ and Percoll). The gradients were centrifuged in a swing-out rotor at 10,000×g for 10 min at 4° C. The intact chloroplast band near the bottom of the gradient was collected and diluted at least five fold with 1×HS buffer (50 mM HEPES-KOH pH 8.0, 0.33 M sorbitol). The intact plastids were collected by centrifugation at 4,350×g for 2 minutes. This step was then repeated once more with the pelleted chloroplasts by resuspending in 1×HS. The final pellet was resuspended in 5 ml of 1×HS and an aliquot subjected to chlorophyll analysis. Chlorophyll assays were performed as described by Arnon (1949) *Plant Physiol.* 24: 1. Samples were extracted with 80% acetone/20% water (v/v). Insoluble material was removed by centrifugation in a microfuge for 1 minute at high speed. The supernatant was removed for spectrophotometric analysis of chlorophyll according to the Arnon conversion equation. Chloroplast envelopes were subfractionated using the freeze-thaw method and discontinuous or flotation sucrose gradients according to Cline et al. (1985) *J. Biol. Chem.* 260:3691 or Keegstra and Yousif (1986) *Methods Enzymol.* 118:316. The final pellet of intact chloroplasts was collected by centrifugation as before and resuspended in a hyperosmotic solution of 0.6 M sucrose, 10 mM Tricine-NaOH pH 7.5 and 2 mM EDTA. Rupturing of chloroplasts was facilitated by one cycle of freezing for 1.5 hour at –20° C. and thawing at room temperature. A crude envelope fraction was collected by diluting with 2 volumes of 10 mM Tricine-NaOH pH 7.5, 2 mM EDTA, centrifuging at 4,500×g for 15 minutes to remove the bulk of thylakoids and then recentrifuging the supernatant at 40,000×g for 30 minutes. The crude envelope pellet was then resuspended in 0.2 M sucrose, 10 mM Tricine-NaOH pH 7.5, 2 mM EDTA buffer for discontinuous sucrose gradients. The discontinuous sucrose gradients consisted of 3 ml of 1.0 M sucrose, 3 ml of 0.8 M sucrose and 3 ml of 0.46 M sucrose (all sucrose solutions were made in 10 mM Tricine-NaOH pH 7.5, 2 mM EDTA buffer). The resuspended crude envelope mixture (approximately 2.5 ml in volume per gradient) was then overlaid onto the discontinuous gradient and centrifuged at 180,000×g for 2 hours at 4° C. in a swing-out rotor. The outer and inner envelope fractions were collected from the corresponding interfaces. The outer membrane fraction was located in the 0.46/0.8 M interface and the inner membrane fraction was in the 0.8/1.0 M interface. These fractions were diluted at least five volumes with Tricine-EDTA buffer, and collected by centrifugation as described for the pelleting of crude envelope preparations. Alternatively, the ruptured chloroplasts can be readjusted to 1.3 M sucrose using a 2.6 M sucrose solution if flotation gradients are used. This mixture (approximately 15 ml) was then overlaid with 9 ml of 1.2 M sucrose and 6 ml of 0.3 M sucrose (all made in Tricine-EDTA buffer as above). The resulting gradients were then centrifuged at 113,000×g for 10–14 hours at 4° C. Total envelopes were collected from the 0.3/1.2 M interface, diluted with Tricine-EDTA buffer and pelleted by centrifugation as described above. All envelope membrane preparations were stored in Tricine-EDTA buffer at −70° C. until use. Total mixed outer and inner chloroplast envelope preparations were used for the immunization protocols. Approximately 50–100 µg of total envelope protein was used for each iomunization injection.

Example 2
Antibody preparations

Monospecific type G immunoglobulins used in the various immunological experiments were prepared using female New Zealand white rabbits according to Chua et al. (1982) In: *Methods in Chloroplast Molecular Biology* (Edelman, M., Hallick, R. B., Chua, N. H., eds.) pp.1063–1080. Elsevier Biomedical Press, Amsterdam. The polyclonal antiserum initially used in the identification of cDNA clones encoding Com44/Cim44 (Bce44B is a member of the Com44/Cim44 protein family) was raised against total pea chloroplast envelope proteins as previously described in Ko, K. et al. (1992) *J. Biol. Chem.* 267:2986. Antibodies against the COOH terminus of the tomato 44 kDa envelope protein (Tce44) and both NH$_2$ and COOH termini of the *Brassica napus* 44 kDa envelope protein (Bce44B) were generated as outlined in Wu et al. (1994) *J. Biol. Chem.* 269:32264. These proteins were generated using the T7 RNA polymerase-expressing bacterial overexpression system. The plasmid vector pGEMEX-1 (Promega) and *E. coli* strain JM109 (DE3) were used to facilitate overexpression. Protein inclusion bodies were purified according to a procedure in Sambrook et al. (1989) *Molecular Cloning: A Laboratory Manual*, Cold Spring Harbor Laboratory, Cold Spring Harbor, N.Y. Denatured fusion proteins (pGEMEX-1 foreign protein segments fused to T7 gene 10 protein) were prepared and purified by preparative SDS-PAGE prior to extraction and electroconcentration. Approximately 25 µg of antigens were used for each booster injection. Each injection in addition contained saline solution (150 mM sodium chloride and 10 mM phosphate buffer pH 7.0), 0.1% SDS (w/v) and RIBI adjuvant (RIBI Immunochem Research Inc, Hamilton, Mont.). A total volume of 500 µl was injected each time. The initial immunization program occurred over a six-week period and the rabbits were given monthly boosters a week prior to bleeding. Preimmnune sera and corresponding IgGs were collected and purified prior to the injection of each rabbit.

Example 3
Identification of CDNA clones encoding 44 kDa proteins

Construction of the Brassica napus (cv. Topas) cDNA expression library and the strategy for immunoscreening the *B. napus* cDNA expression library were performed as described in Ko, K. et al. (1992) *J. Biol. Chem.* 267:2986 and Ko, K. et al., (1994) *Plant Physiol.* 104:1087. The cDNA expression library was constructed in the phage vector λgt22 (Promega) using polyadenylated RNA isolated from 21 day old *Brassica napus* (cv. Topas) developing seeds. The synthesis of cDNA was facilitated using a kit purchased from Promega. The growth and propagation of the cDNA library was performed according to standard methods such as the ones described in *Molecular Cloning: A Laboratory Manual* (Sambrook et al. (1989) Cold Spring Harbor Laboratory, Cold Spring Harbor, N.Y.). The cDNA inserts were retrieved by an EcoRI-NotI digestion from the selected appropriate recombinant phage DNA and subcloned into pGEM 11Z (Promega) for expression in JM109(DE3) and for further analysis.

Example 4
Nucleotide sequence analysis

The nucleotide sequence of the Bce44B cDNA insert was determined by the standard dideoxynucleotide chain-termination method using double-stranded DNA templates (*Molecular Cloning: A Laboratory Manual*, Sambrook et al., (1989) Cold Spring Harbor Laboratory, Cold Spring Harbor, N.Y.).

Example 5
Protein analysis

All proteinaceous samples were resolved and analyzed by denaturing SDS-PAGE (Laemmli, (1970) *Nature* 227:680; Towbin et al. (1979) *Proc. Natl. Acad. Sci. USA* 76:4350), electrophoretically transferred onto nitrocellulose filters and immunologically analyzed as described by Hoffman et al. (1987) *Proc. Natl. Acad. Sci. USA* 84:8844. Primary immunoreactions were detected using alkaline phosphatase-conjugated anti-rabbit IgGs (Sigma; Promega). The resulting immunoblots were analyzed and normalized by laser densitometry using the LKB ULTRASCAN XL laser densitometer and the software GELSCAN.

Example 6
Construction of Bce44B expression plasmid

All DNA cloning and expression plasmids discussed were propagated in the *Escherichia coli* strains HB101 or the JM101–109 strain series. The transformation of various bacterial strains was canied out using standard protocols (such as the ones described in *Molecular Cloning: A Laboratory Manual*, Sambrook et al. (1989) Cold Spring Harbor Laboratory, Cold Spring Harbor, N.Y.). Plasmid DNAs were isolated from the bacterial strains harboring the corresponding plasmids using standard protocols (such as the ones described in *Molecular Cloning: A Laboratory Manual*, Sambrook et al., 1989). Gene constructs that express the Bce44B protein can be created, inserted and propagated in a variety of noncommercial or commercially-available plasmids such as the pBLUESCRIPT series (Stratagene), the pBS series (Stratagene), the pGEM and pSP series (Promega) and pT7/T3 series (Pharmacia) if the T7 RNA polymerase bacterial expression system is used to synthesize Bce44B protein. The T7 RNA polymerase gene in the appropriate bacterial strains such as JM109(DE3) or BL21

(DE3) is under the control of the IPTG-inducible lac promoter. The currently used promoter for expression in the T7 RNA polymerase containing/expressing bacteria is the T7 promoter. Termination sequences such as the T7 terminator can be used in addition to any functionally equivalent sequences present in the gene itself. Other expression systems such as the IPTG-inducible system based on the lac promoter can also be used to express the Bce44B protein, for example, the pKK233 series (Clontech) or the pPROK series (Clontech). Any other bacterial expression system that causes the expression of the Bce44B protein in a desirable manner including constitutive expression can also be used. Plasmids usually contain multiple cloning regions for cloning manipulations, an origin of replication and a selectable gene marker such as antibiotic resistance. Expression plasmids additionally contain an appropriate promoter.

All restriction endonuclease digestions were carried out in accordance with the buffers and protocols provided by the manufacturer of each particular enzyme. Restriction enzyme was added to give 5–10 units per microgram of DNA and the reaction mixture was adjusted to the appropriate final volume with water. The final volumes were usually 20–100 μl and contained 2–10 μg of plasmid DNA. Digestions were thoroughly mixed and carried out for 1 hour at the appropriate suggested temperature. Digested DNA molecules were re-purified by phenol and chloroform:iso-amyl alcohol extraction, centrifugation (usually in a microfuge) and the aqueous layer containing the digested DNA concentrated by precipitation in two volumes of 100% ethanol in the presence of 0.3 M sodium acetate, pH 7.0 or 0.1 M sodium chloride. The phenol used was saturated with 0.1 M Tris-HCl pH 8.0 plus 0.1% (w/v) hydroxquinoline prior to use. The chloroforn:iso-amyl alcohol consisted of 24 volumes of chloroform and 1 volume of iso-amyl alcohol. Equal volumes of phenol or chloroform:iso-amyl alcohol were used in each of the organic solvent extraction steps. The DNA precipitates were collected by centrifugation, washed once with 70% ethanol (70% ethanol, 30% water), dried and redissolved in an appropriate volume of water prior to further manipulations.

The Bce44B expression plasmid was made by first retrieving the 1193 base pair cDNA insert from the recombinant phage DNA described above. Retrieval was achieved by EcoRI and NotI restriction enzyme digestions. The purification of the cDNA insert was carried out using the standard low melting agarose gel and phenol extraction method (*Molecular Cloning: A Laboratory Manual*, Sambrook et al., (1989) Cold Spring Harbor Laboratory, Cold Spring Harbor, N.Y.). The low melting agarose was supplied by GIBCO-BRL, Gaithersburg, Md., U.S.A. DNA was recovered from appropriate low melting agarose slices by heating at 65° C. followed by extraction with phenol that had been prewarmed at 37° C., and centrifuigation. The phenol extraction was repeated. The aqueous layer containing the DNA was then adjusted to 0.1 M sodium chloride and centrifuged for 10 min in a microfuge. The supernatant was then given a chloroform:iso-amyl alcohol extraction followed by precipitation in ethanol as described above. The DNA pellet was then collected by centrifugation, washed with 70% ethanol, dried and resuspended in water. The pGEM11Z plasmid was digested with the same enzymes and dephosphorylated. Phosphatase reactions were carried out by adjusting the restriction digestion reactions with 3.5 μl IM Tris-HCl, pH 8.0 (per 100 μl reaction) and adding 0.5 unit of calf intestinal alkaline phosphatase. Incubation proceeded for 30 minutes at 37° C. and the DNA was then repurified by organic solvent extraction followed by ethanol precipitation as above.

The pOee1-Dhfr plasmid encoding a chimeric chloroplast protein presursor (Wu, C. and Ko. K (1993) *J. Biol. Chem.* 268:19384–19391) was constructed in the same manner using the same expression vector as pBce44B except that the gene encoding Oee1-Dhfr replaced the gene encoding Bce44B. Plasmid pOee1-Dhfr was used as the expression control plasmnid.

The ligation reactions consisted of the two appropriate target DNA molecules, ligase buffer (50 mM Tris-HCl pH 7.5, 10 mM magnesium chloride, 1 mM dithiothreitol, 1 mM ATP) and 1–3 units of enzyme. The ligation reaction was carried out at 15° C. using T4 DNA ligase from various suppliers. See, e.g., Sambrook et al., supra.

Example 7

Construction of the truncated Bce44B expression plasrids

Carboxyl-terminal deletions of Bce44B were created by exonuclease III/S1 digestion (Henikoff, (1987) *Meth. Enzymol.* 155:156. The resulting truncated products of these deletion constructs (designated C1–C5) lacked 10, 24, 197, 234 and 284 amino acids from the COOH terminus, representing deletions of 3, 7, 60, 72 and 80% of the Bce44B protein, respectively. All of these constructs were subcloned into the EcoRI and SmaI sites of pGEM4. The DNA fragments generated by deletion possessed a blunt end and an EcoRI end.

Amino-terminal deletions of Bce44B were generated by exonuclease III/S1digestion and joining the digested DNA fragments to the DNA sequence for the first 4 amino acids of the RbcS transit peptide (MASM) from *Pisum sativum*. This cloning strategy is similar to that reported earlier (Wu and Ko, (1993) *J. Biol. Chem.* 268:19384; Ko and Cashmore (1989) *EMBO J.* 8:3187). The resulting translation products of these deletion constructs (designated N1–N4) lacked 42, 82, 140 and 181 amino acids from the $NH_2$ terminus. The amino acid sequences of the fusion site of N1–N4 are MASMISSLSVPPQ-, MASMISSLSVPPSV-, MASMISSLSRLF- and MASMMYPKMI-, respectively. All of these deletion constructs (N1–N4) were made in pGEM4. The N1 deletion construct was then subcloned into the same plasmid vector as employed for Bce44B and the resulting recombinant plasmid was designated pK117. See Example 18.

The K118 fusion construct was made by joining the DNA sequence for the first 23 amino acids of Bce44B to N1. The DNA fragment encoding the $NH_2$-terminal 23 amino acids and the 5' untranslated region of Bce44B was retrieved from C5 using EcoRI and HinfI. The EcoRI-HinfI DNA fragment was inserted into pGEM4 via EcoRI and SmaI, after first converting the HinfI site to a blunt end using the Klenow fragment of *E. coli* DNA polymerase I. This resulting vector was used for the construction of K118. The K118 fiusion was completed by joining to an Asp718-HindIII DNA fragment retrieved from N1 via the BamHI and HindHI sites of the above vector. (The Asp718 and BamHI sites were first made blunt ends.) The amino acid sequence of the fusion point is -GLGIVPP-. The fusion construct was subcloned in pGEM4 and then transferred to the same expression plasmid as described above. The final recombinant plasmid was named pK118.

Example 8

Expression of Bce44B in *E. coli*

The expression plasmid pBCE44B was transformed into the *E. coli* strain JM109(DE3) using standard calcium chloride methods. Selected colonies were checked for the presence of the plasmid and its quantity in the cell. The resulting strain of JM109(DE3) containing pBCE44B plasmid was recovered and stored in glycerol stocks at −70° C. or −20° C. until use. The glycerol stocks were made by taking 750 μl of log phase growing cells and mixing in 150 μl of sterile glycerol.

For each expression experiment, the cells were streaked out on LB-ampicillin plates (25 μg/ml) and incubated at 37° C. overnight. Colonies formed on the overnight plate were then used to inoculate a liquid culture of LB and ampicillin. Incubation again proceeded with shaking overnight at 37° C. This overnight liquid culture was then used to inoculate a culture to induce expression of Bce44B. The overnight liquid culture was used as an inoculum at a ratio of 1/100 and the freshly inoculated culture allowed to grow with shaking for 2 hours at 37° C.

Induction of expression was achieved by the addition of 10 ILI of isopropyl B-D-thiogalactopyranoside (IPTG) (48 mg/ml stock) two hours after inoculation. Lower but sufficient levels of expression can also be obtained without IPTG induction. Expression was allowed to proceed for another 2–3 hours before the cells were collected by centrifugation.

The pelleted cells were then resuspended in SDS-PAGE loading buffer (5% SDS (w/v), 0.1% bromophenol blue (w/v), 20% glycerol (v/v), 1.2 M β-mercaptoethanol, 0.1 M Tris-HCl pH 6.8), boiled for 3 minutes, and centrifuged for 5 minutes in a microfuge before loading onto an SDS-polyacrylamide gel for analysis. Protein gels were visualized by Coomassie Blue staining or more specific protein bands were analyzed by immunoblotting with various specific antibodies as described above.

Example 9

E. coli inner and outer envelope membrane subfractionation

Subfractionation of bacterial membranes was carried out according to Cabelli et al. (1991) *J. Biol. Chem.* 266:24420. Cells were grown in LB broth containing 25 μg/ml of ampicillin to $O.D._{600}$=0.8–1.0, pelleted by centrifugation in a JA-20 rotor (Beckman) at 7,000 r.p.m. at 4° C., and resuspended in cold 20% sucrose (w/v) in 10 mM Tris-HCl pH 8.0, 150 μg/ml DNase I+150 μg/ml RNase. Cells were then broken twice at a setting of 15,000 p.s.i. in a French Pressure cell. Broken cells were then chilled on ice. Cell debris was removed by centrifugation at 3,000 r.p.m. for 10 min at 4° C. in a Beckman JA-20 rotor. The resulting supernatant was subjected to the two-stage separation of the membrane fractions.

Whole membranes were first collected by a low density sucrose gradient consisting of 5 ml 70% sucrose, 12 ml 18% sucrose overlaid with 20 ml of broken cell supernatant in a polyallomer tube. The samples were centrifuged at 23,000 r.p.m. in a SW27 or SW28 rotor (Beckman) for 2 hours at 4° C. Outer and inner membranes banded at the junction between the 18% and 70% steps and were carefully collected using a glass pipette. The collected whole membrane fraction was subjected to further separation into OM1, OM2, M, and IM by using a 4-step gradient consisting of 3 ml 70% sucrose, 9 ml 64% sucrose, 9 ml 58% sucrose, 9 ml 52% sucrose, and 7 ml of sample. The whole membrane fraction was layered on the top, centrifuged for 4 hours to overnight at 23,000 r.p.m. in a SW27 or SW28 rotor (Beckman) at 4° C. Four bands appeared upon completion of centrifuigation; the upper two were reddish, and the lower two were whitish. The lower bands were outer membranes (OM). Bands were carefully collected as separate fractions using a glass pipette. Each collected band was placed in 70Ti polycarbonate tube and diluted with at least 2 volumes of distilled water (to dilute the sucrose concentration to below 20%), then centrifuged at 47,000 r.p.m. at 4° C. for 60 minutes in a Beckman Ti 70 rotor. The pellets were resuspended in 50 mM Tris-HCl (pH 7.0) and stored at −80° C. until analysis.

The purity of fractions of the inner and outer membrane was determined by detection of cytochrome b1 content, which is mainly in the inner membrane fraction, and of KDO (2-keto-3-deoxyoctonate) content of the peptidoglycan, which is mainly in the outer membrane fraction, using the methods of Deeb and Hager (1969) *J. Biol. Chem.* 239:1024 and Braun and Rehn (1969) *Eur. J. Biochem.* 10:426, respectively. Outer and inner membrane fractions were also analyzed by SDS-polyacrylamide gel electrophoresis and silver staining, confirming the identity of the membrane fractions by visualizing the distinct protein profiles of the two different fractions.

Example 10

Preparation of RSO membrane vesicles

Right-side-out (RSO) vesicles were obtained by the method described in Kim et al. (1994) *Cell* 78:845. Cells were harvested by sedimentation and washed twice in 30 mM Tris-HCl (pH 7.5), 20% sucrose, 1 mM phenylmethyl-sulfonyl fluoride (PMSF). EDTA (pH 8.0) and lysozyme were added to final concentrations of 10 mM and 0.5 mg/ml, respectively. The cells were then incubated for 40 minutes at 4° C. All subsequent manipulations were performed at 4° C. Spheroplasts were sedimented at 16,000×g for 15 minutes, and pellets were resuspended in the smallest possible volume (0.5–1.0 ml) of 0.1 M Tris-HCl (pH 7.5), 20% sucrose, 20 mM magnesium sulfate, 1 mM PMSF containing DNase and RNase at concentrations of 3–5 μg/ml, using a Teflon and glass homogenizer. The suspension was poured into 300–500 vol. of 50 mM Tris-HCl (pH 7.5), 1 mM PMSF and incubated for 15 minutes, when EDTA (pH 8.0) was then added to 10 mM, and incubation was continued for an additional 15 minutes. $MgSO_4$ was added to 15 mM, and incubation was continued for an additional 15 minutes. The lysate was sedimented at 16,000×g for 30 min, and the pellet was resuspended by vigorous homogenization in a solution of 50 mM Tris-HCl (pH 7.5), 10 mM EDTA, 1 mM PMSF. This preparation was sedimented at 45,000×g for 20 minutes, and the pellet was resuspended by homogenization in 50 mM Tris - HCl (pH 7.5), 10 mM EDTA, 1 mM PMSF. The sample was sedimented at 800×g for 30 min, and the yellowish, milky supernatant fluid was carefully decanted and sedimented at 45,000×g for 20 minutes. Low speed sedimentation was repeated on the 800×g pellet fraction after the extensive homogenization in order to obtain a maximal yield of RSO membrane vesicles. The resulting RSO samples were resuspended into aliquots, and stored at −80° C. until use.

Example 11

Preparation of ISO membrane vesicles

Inside-out (ISO) vesicles were prepared according to Kim and Oliver (1994) *FEBS Lett.* 339:175. Cells were harvested by sedimentation, washed once in 50 mM Tris-HCl (pH 7.5), 5 mM $MgSO_4$ at 6 ml/g wet weight of cells, and DNase I was added to 10 μg/ml. The cell suspension was passed through the French Pressure cell twice at 5,000 p.s.i. Unbroken cells were removed by sedimentation at 10,000×g for 10 minutes, and a membrane pellet was obtained after sedimentation at 12,000×g for 2 hours. Membranes were resuspended in 50 mM Tris-HCl (pH 7.5), 1 mM dithiothreitol, 10% glycerol, and 250 mM sucrose and stored at −80° C. until use.

Example 12

Thermolysin digestion of ISO and RSO membrane vesicles

Both RSO and ISO membrane vesicles were adjusted to 3 mg protein/ml in the washing buffers: 50 mM Tris-HCl (pH 7.5) for RSO membrane vesicles; 50 mM Tris-HCl (pH 7.5), 1 mM dithiothreitol, 10% glycerol, 250 mM sucrose for ISO membrane vesicles. Reactions were initiated by adjustment to 0.5 mg of thermolysin/ml prepared in 50 mM Tris-HCl (pH 7.5) containing 1 mM $CaCl_2$. The protease treatment scheme was performed as reported by Cline et al. (1984) *Plant Physiol.* 75:675. After incubation on ice for 25 minutes, reactions were terminated by adjusting reaction mixtures to 10 mM EDTA. Control vesicles were subjected to the same treatment with the exception that control vesicles did not receive thermolysin. Triton X-100 was added to a final concentration of 0.1% to one thermolysin digestion group, as another control. An equal volume of 2×SDS loading buffer was then added to the reaction mixtures. Samples were boiled for 3 minutes, separated by 10% SDS-polyacrylamide gel electrophoresis and inmmunoblotted with specific anti-Bce44B protein antibodies.

Example 13
Induction and transport of alkaline phosphatase in *E. coli* JM109 (DE3)

The induction and analysis of alkaline phosphatase was performed as described by Torniani et al. (1960) *Biochim. Biophys. Acta.* 38:460. Bacterial cells were grown in LB-ampicillin (25 μg/ml) broth till $O.D._{600}$=0.8–1.0, diluted 50× into M9 minimal broth (0.06 M $K_2HPO_4$, 0.03 M $KH_2PO_4$, 7.5 mM $(NH_4)_2SO_4$, 2 mM sodium citrate.$2H_2O$, pH 7.0) and in M9 (-$P_i$) broth (phosphate starvation broth) which was identical to the M9 minimal broth except that it contained 0.15 M Tris instead of phosphates. Both media contained 0.1% glucose, 0.2% glycerol, and 1 mM twenty amino acid mixture as additional components. A low concentration of phosphate (50 μM) was present in the M9 (-$P_i$) minimal broth to provide enough essential phosphorus for cell growth. Cells were collected at 10 hour and 15 hour growing periods and adjusted to the same cell number by using the $O.D._{600}$. values. Samples were then processed in 1×SDS loading buffer, subjected to 10% SDS-polyacrylamide gel electrophoresis and immunoblotted with anti-alkaline phosphatase antibodies to visualize the alkaline phosphatase profiles in both Bce44B-expressing and Oee1-Dhfr-expressing cells.

The results showed that Bce44B-expressing cells grow more slowly than the Oee1-Dhfr-expressing cells even under normal phosphate levels. In the M9 minimal as media with 50 μM phosphate (phosphate starvation levels), the Bce44B-expressing cells gave rise to two peaks (10 and 15 hours) during the growing period. Immunoblots were made comparing the amount of processed alkaline phosphatase from the two types of cells at the time of the two growth peaks both with and without phosphate starvation.

Example 14
Analysis of changes in the transport of β-lactamase

Changes to β-lactamase transport were monitored by two different approaches: 1) the ability to form colonies on solid LB-agar plates containing increasing concentrations of ampicillin (50 μg/ml to 3.0 mg/ml); and 2) the level of transported and processed β-lactamase detected by immunoblotting total protein samples of cells grown in LB-broth containing increasing ampicillin concentrations.

Bce44B- and Oee1-Dhfr-expressing cells were grown in LB broth containing 25 μg/ml ampicillin to $OD_{600}$=0.8–1.0. Cultures were collected and $OD_{600}$ values measured to adjust by dilution the cell numbers (usually 500–700 cells) to approximately the same numbers before plating onto LB agar plates containing increasing amounts of ampicillin. Plates were incubated at appropriate temperatures overnight. Colony numbers on each plate with increasing ampicillin concentrations were compiled and compared to assess the level of ampicillin resistance based on the ability to form colonies.

The same cells were also used to determine the level of transported β-lactamase grown in media containing increasing concentrations of ampicillin. Cultures were diluted 5× into LB broth with increasing amounts of ampicillin (50 μg/ml to 3.0 mg/ml) and allowed to grow up to 4 hours. The level of transported β-lactamase was monitored by immunoblotting analysis of samples taken at time intervals of 0 hr, 0.5 hr, 1.0 hr, 1.5 hr, 2.0 hr, 3 hr and 4 hr. Immunoblot analysis was performed on total cellular protein samples with anti-p-lactamase antibodies as outlined above.

Example 15
Sodium azide sensitivity analysis

Sensitivity of the bacterial strains to sodium azide was determined in the same manner as outlined in Oliver el al. (1990) *Proc. Natl. Acad. Sci. USA* 87:8227. Changes to β-lactamase transport activity in response to sodium azide was used as a monitor of differences in the protein translocation activity of Bce44B- versus Oee1-Ohfr-expressing cells. Both Bce44B-expressing and Oee1-Dhfr-expressing cells were grown in LB broth with an ampicillin concentration of 25 μg/ml till $O.D._{600}$=0.8–1.0, diluted 50× into the LB broth containing increasing concentrations of sodium azide (0 to 1.0 mM) and incubated for 2.0 hours. Samples were then adjusted to the same cell numbers by measuring $O.D._{600}$. values at the time of collection, subjected to 10% SDS-PAGE and immunoblotted with anti-β-lactamase antibodies (5 PRIMES→3 PRIME, Inc., Boulder, Colo.).

The same strains were also assessed using 0.5 mM sodium azide over a period of 2.0 hours. The time course study was tamed out in the same manner as above where the cells were inoculated in LB-ampicillin broth containing 0.5 mM sodum azide. Samples were collected and monitored by immunoblotting at time intervals of 0, 0.5, 1.0, 1.5 and 2.0 hr as outlined above. Control experiments were conducted without sodium azide.

Example 16
Preparation of spheroplasts and chemical cross-linking studies

The chemical cross-linking of bacterial proteins was performed as described by Akita et al. (1990) *J. Biol. Chem.* 265:8164. The Bce44B-expressing cells and Oee1-Dhfr-containing cells were grown to $O.D._{600}$=0.8–1.0, harvested by sedimentation at 3,000×g for 5 minutes, washed twice in 30 mM Tris-HCl (pH 7.5), and resedimented by centrifuigation as above. The cells were resuspended in ice-cold 30 mM Tris-HCl (pH 7.5), 20% sucrose, 1 mM PMSF, 10 mM EDTA (pH 8.0), and 0.5 mg/ml lysozyme, followed by incubation for 40 minutes at 4° C. The resulting spheroplasts were sedimented at 16,000×g for 15 minutes, washed twice with 20% sucrose, 20 mM HEPES-NaOH (pH 7.7) and resuspended in the same buffer. The chemical crosslinker, EDAC (1-ethyl-3-(3-dimethylaminopropyl) carbodiimide methiodide), was then added to a concentration of 12.5 mM. The cross-linking reaction was carried out at 25° C. for 50 minutes, and quenched for 10 minutes by the addition of 200 mM Tris-HCl (pH 7.5). The cross-linked complexes were resolved by 10% SDS-polyacrylamide gel electrophoresis and immunoblotted separately with specific antibodies against the tetracycline efflux protein, Tet, Bce44B and β-lactamase.

Immunoblots of the cross-linked complexes of the Bce44B-expressing cells showed that a high molecular weight cross-linking-generated band of approximately 70 kDa immunoreacted with antibodies against Bce44B and β-lactamase.

Example 17

Complementation analysis of Bce44B and secA mutant bacterial strain

The pBCE44B and pOEEIDHFR plasmids were introduced into *E. coli* strain MM52 (Oliver and Beckwith, (1981) *Cell* 25:765) by electroporation using the BioRad Gene Pulser and the supplied protocols for *E. coli* strains. Electrocompetent cells were prepared according to the supplied protocol. The MM52 strain is a derivative of MC4100 with a characterized temperature-sensitive mutation in the secA gene, which encodes a component of the bacterial protein secretory machinery. The mutation is termed secATs51. The plasmid-harboring MM52 strains were grown in LB-ampicillin broth and analyzed in the same manner as the JM109(DE3) strains described above.

Example 18

Characterization of bacterial strains harboring truncated Bce44B

Figure 4:
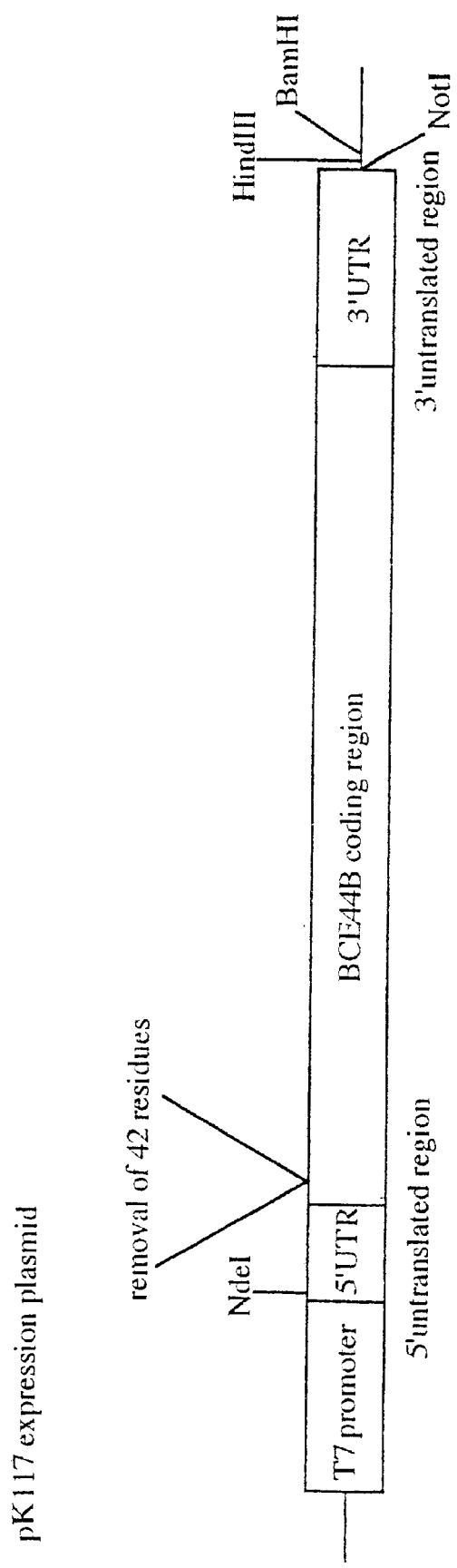
FIG. 4 is a diagram of a truncated Bce44B expression plasmid pK117.
Figure 5:
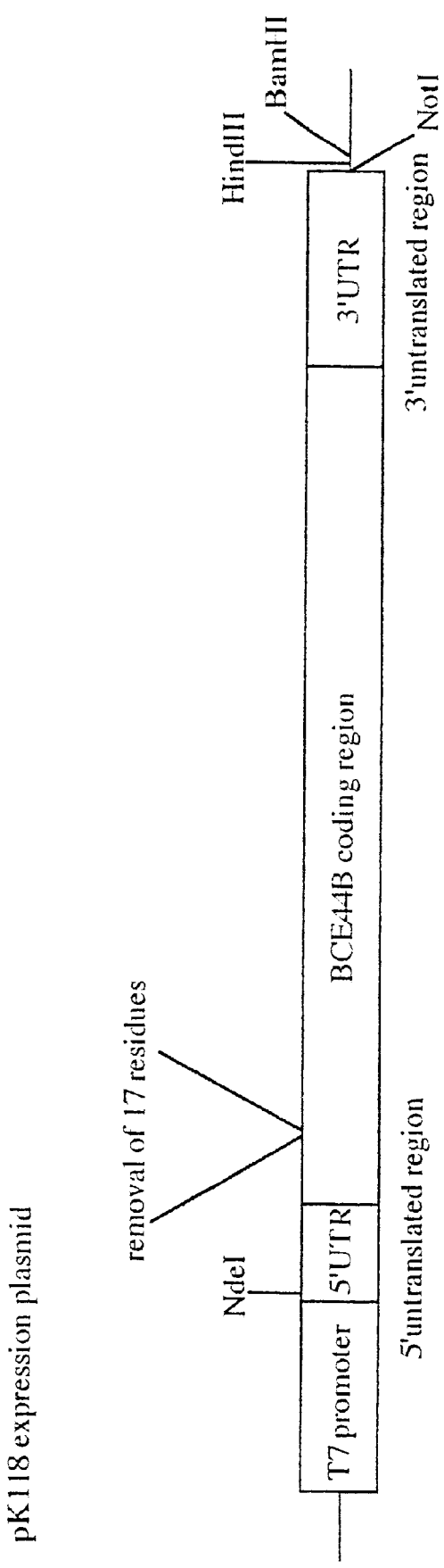
FIG. 5 is a diagram of a truncated Bce44B expression plasmid pK118.

The pk117 ana pK118 plasmids, FIGS. 4 and 5, respectively, were introduced into *E. coli* strain JM109 (DE3) and analyzed using the same criteria as described above for the Bce44B-expressing strains.

Example 19

Construction of a CaMV-Bce44B-NOS Transgene for Expression in Plants

Transgenic plants (*Brassica napus, Arabidopsis thaliana* and *Lycopersicon esculentum*) with altered plastid protein transport capacity were produced by introducing a transgene construct consisting of DNA encoding the Bce44B protein and a 5' untranslated region immediately upstream of the Bce44B coding sequence. See FIG. 6. Expression of the construct was obtained by linking the cauliflower mosaic virus 35S promoter (Odell, J. T. et al. (1985) *Nature* 313:810) upstream. Transcriptional termination was facilitated by the gene encoding nopaline synthase (NOS) found in Agrobacterium Ti plasmids or their derivatives such as pBI101 (Clontech). Construction of the 35S CAMV-Bce44B-NOS transgene construct is diagrammed in FIG. 6.

Figure 6:
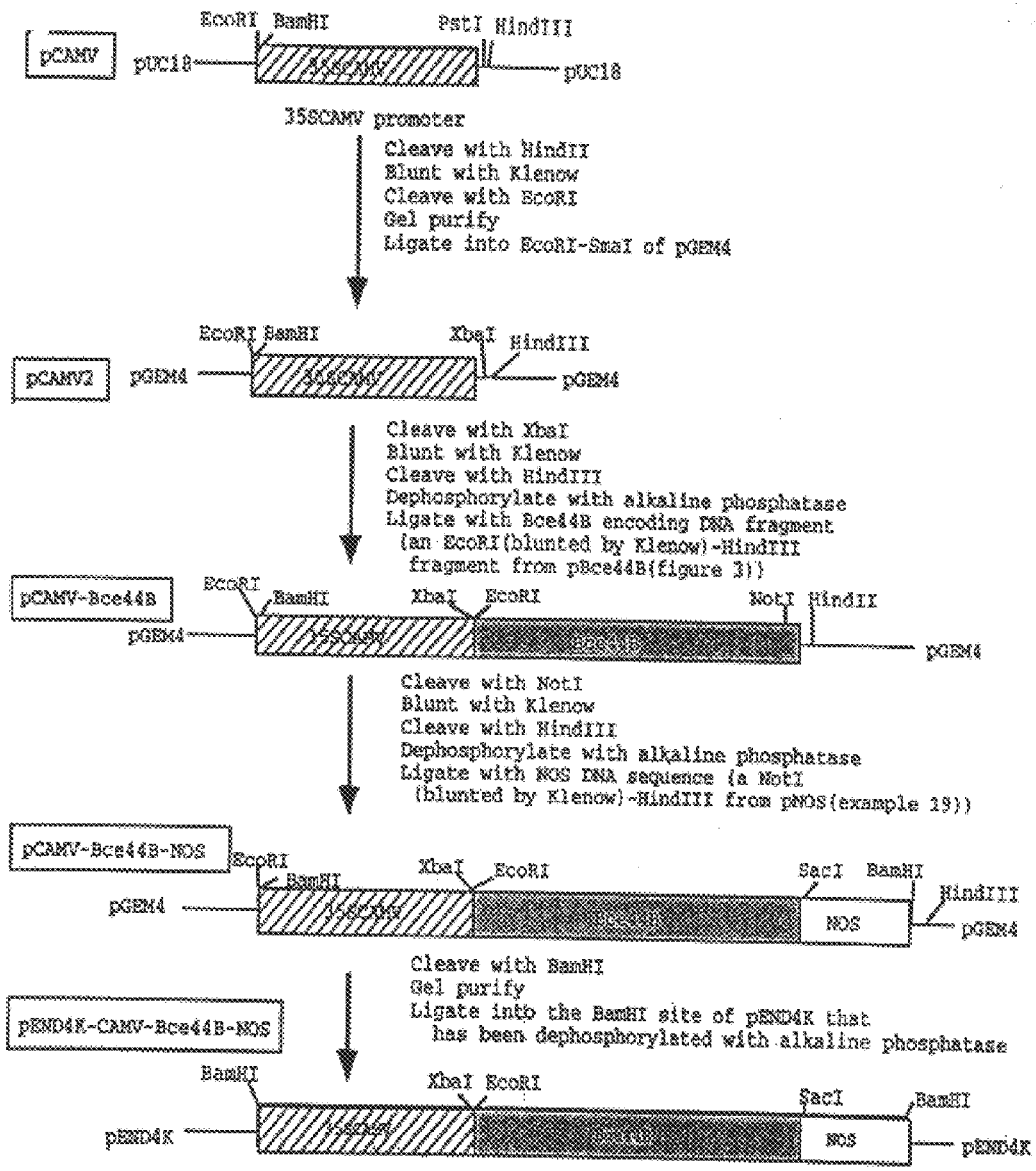
FIG. 6 is a diagram of the construction of the CAMV-Bce44B-NOS transgene.

The transgene cloning process was initiated by the construction of a vector containing DNA encoding the 358 CAMV promoter. The DNA cloning procedures generally used have been described in the examples supra. The 35S CAMV constitutive promoter was retrieved as an EcoRI-HindIII DNA fragment (approximately 450 base pairs in length) from pCAMV (A. R. Cashmore, Univ. Pennsylvania, Philadelphia, Pa.). The HindIII restriction site was converted to a blunt end with Klenow fragment and the DNA fragment inserted into the EcoPI and SmaI sites of pGEM4 (Promega). This vector, designated pCAMV2, was used to fuse the 35S CAMV promoter to the Bce44B coding region by retrieving Bce44B as a 1,193 base pair EcoRI-HindIII DNA fragment from pBce44B (FIG. 3) and inserting it into the XbaI-HindIII sites of pCAMV2. The EcoRI and XbaI sites were made into blunt end sites using Klenow fragment and the resulting vector was designated pCAMV-Bce44B (FIG. 6). The 3' transcription termination sequence from the NOS gene was then added to the linked pCAMV and Bce44B sequences by inserting an EcoRI-HindRI DNA fragment (approximately 260 base pairs in length) into the NotI-HindIII sites of pCAMV-Bce44B, following which the EcoRI and NotI sites were made blunt using Klenow fragment. The NOS transcription termination sequence was retrieved from the pBI121 binary vector (Clontech) as a SacI-EcoRI DNA fragment (approximately 260 base pairs in length). To obtain the appropriate restriction sites for insertion of the NOS transcription termination sequence into pCAMV-Bce44B, the SacI-EcoRI DNA fragment was first inserted into the SacI-SmaI sites of pGEM4 (this vector was designated pNOS for reference purposes) and then retrieved back out as the EcoRI-HindIII DNA fragment described above. The resulting transgene-containing vector was designated pCAMV-Bce44B-NOS (FIG. 6). The 35SCAMV-Bce44B-NOS transgene was then transferred as a BamHI DNA fragment from pCAMV-Bce44B-NOS to the BamIH site of the binary vector pEND4K (Klee, H. et al. (1985) *Biotechnology* 3:637; Horsch, R. B. et al. (1985) *Science* 227:181; Holsters, M. et al. (1987) *Mol. Gen. Genet.* 163:181). The trnsgene-containing Agrobacterium binary vector was designated pEND4K-CAMV-Bce44B-NOS (FIG. 6).

All ligation steps were carried out at 15° C. overnight using T4 DNA ligase from various suppliers. All steps of the gene construction process were carried out using the standard $CaCl_2$ bacterial transformation protocol and the *E. coli* host strain HB 101. The recombinant plasmids were propagated in HB101 and isolated using standard techniques. Resolution of DNA fragments was facilitated by using standard agarose and polyacrylamide gel electrophoresis techniques. See, Sambrook et al., supra.

Example 20

Transformation of Plants

The pEND4K-CAMV-Bce44B-NOS vector was introduced into *Agrobacterium tumafaciens* by the freeze-thaw method. Competent Agrobacterium strains (such as LBA4404 or GV3101) were obtained by inoculating 50 ml of LB broth containing the appropriate antibiotics (50µg/ml rifampicin for LBA4404 or 100 µg/ml gentamycin and 150 µg/ml rifampicin for GV301) with 500 µl of an overnight culture, incubating at 28° C. with vigorous shaking until the optical density at 650 nm reached 0.7. Cells were harvested by centrifugation at 2000×g for 5min at 4° C., washed in ice cold 0.1M $CaCl_2$ and finally resuspended in 1 ml of ice cold 20 mM $CaCl_2$. A 150 µl aliquot of competent LBA4404 or GV301 cells was removed, mixed with 1µg of plasmid DNA in a microfuge tube, and immediately frozen in liquid nitrogen. The cells were incubated at 37° C. in a water bath or thermostat block for 5 min, 1 ml of LB broth was added, and the mixture incubated at 28° C. with shaking for 3h. Cells were recovered by centrifugation at 2000×g for 5 min and resuspended in 100 µL of LB before plating on LB plates containing appropriate levels of antibiotics for selection of kanamycin-resistant cells (100 µg/ml kanamycin and 50 µg/ml rifampicin for the LBA4404 strain or 50 µg/ml kanamycin, 150 µg/ml rifampicin and 100 µg/ml gentamycin for the GV3101 strain). After a 2–4 day incubation at 28° C., kanamycin-resistant colonies growing on the plates were selected and the presence of the pEND4K-CAMV-Bce44B-NOS plasmid confirmed in plasmid preparations prepared from single colonies as described below.

Three ml of LB broth containing appropriate levels of antibiotics as described above for the selection process were inoculated with a single kanamycin-resistant colony and incubated from overnight to 2 days at 28° C. with shaking. A 1.5 ml sample of this culture was placed in a microfuge tube and centrifuged for 30 sec to pellet the cells. The pellet was resuspended in 0.1 ml of GTE solution (50 mM glucose, 25 mM Tris-HCl pH 8.0, 10 mM NaEDTA) and 4 mg/ml lysozyme, then incubated at room temperature for 10 min. Phenol (30 µl), previously equilibrated with 2 vols of 1%

(w/v) SDS, 0.2N NaOH, was added. The mixture was vortexed gently until viscous and incubated at room temperature for 10 min. The lysed cells were neutralized with 3M sodium acetate pH 4.8 (150 µl) and incubated at −20° C. for 15 min. The mixture was centrifuged for 3 minutes in a microfuge and the supernatant transferred to a fresh microfuge tube. Two volumes of ethanol were added and the mixture incubated at −80° C. for 15 minutes, prior to centrifuigation for 3 minutes, after which the DNA pellet was resuspended in 90 µl of water. Ten µl of 3M sodium acetate, pH 7.0, were added, then an equal volume of phenol/chloroform, before vortexing the mixture. After a 5 min centrifugation in a microfuge, the supernatant was transferred to a fresh tube and the DNA precipitated by adding 2 volumes of 100% ethanol. Following a 10 min centrifugation, the pellet was washed with 70% ethanol, dried and resuspended in 50 ml of TE (10 mM Tris-HCl pH 8.0, 1 mM Na$_2$EDTA).

Restriction endonuclease digestion analysis and Southern blot analysis of the pEND4K-CAMV-Bce44B-NOS plasmid preparation was carried out in accordance with procedures described in Molecular Cloning: A Laboratory Manual (Sambrook et al., supra).

Agrobacterium strains containing the pEND4K-CAMV-Bce44B-NOS plasmid were used to transform plants following a leaf disc transformation protocol, such as the one described by Horsch et al. (1985) *Science* 227:1229), or by in planta methods which can include the seed transformation protocol reported by Feldmann and Marks (1987) *Mol. Gen. Genet.* 208:1–9, the more recently updated seed transformation protocol described by Feldmann (1992) In: *Methods in Arabidopsis Research*, (eds. C. Koncz, N. H. Chua, J. Schell), pp 274–289) and Chee, P. P. (1994, U.S. Pat. Ser. No. 5,169,770), the vacuum infiltration approach reported by Bechtold, N. et al. (1993) CR *Acad. Sci. Paris/Life Science* 316:118) and the approach employing the inoculation of wound sites in the primary and secondary influorescence shoots (Katavic, V. et al. (1994) *Mol. Gen. Genet.* 245:363). Plants, such as *Lycopersicon esculentum* and *Brassica napus*, used for leaf disc transformation were grown in a greenhouse maintained at 18–24° C. and supplemented with fluorescent and incandescent lights. Young leaves were excised and surface sterilized in 10% (v/v) sodium hypochlorite, 0.1% (v/v) Tween, then rinsed 4 times with sterile, deionized water. From this point on, standard aseptic techniques for the manipulation of the sterile material and media were used. Leaf discs, 6 mm in diameter, were made with the aid of a sterile paper punch and incubated for 10–20 min in a 1:5 dilution of cultures of Agrobacterium harboring the pEND4K-CAMV-Bce44B-NOS construct. Excess bacteria were removed from the leaf discs by briefly blotting on sterile filter paper before the discs were transferred to petri dishes containing "shoot medium" (Horsch et al. (1988) In: *Plant Molecular Biology* (Eds. S. B. Gelvin, R. A. Schilperoot) Kiuwer Acad. Publishers, A5:1–9). Petri plates were sealed with parafilm and incubated in a growth chamber at 24° C. equipped with "grow" mixed fluorescent tubes. After 2 days, Agrobacterium growing on the discs were killed by washing in 500 mg/ml Cefotaxime in liquid "shoot medium" and the discs transferred to fresh "shoot medium" containing 500 mg/ml Cefotaxime and 100 mg/l kanamycin to select for growth of transformed plant cells.

Leaf discs were incubated for 3–5 weeks under the same conditions and transferred to fresh medium on a weekly basis. Green shoots emerging from the leaf discs were excised and transferred to "root medium" containing appropriate plant species-specific levels of kanamycin (Horsch et al. (1988), supra). Shoots which rooted in the presence of kanamycin were selected for filrther propagation and for further verification via a variety of approaches including the assessment of NptII activity (McDonnell, R. E. et al. (1987) *Plant Mol. Biol. Rep.* 5:380), polymerase chain reaction techniques to detect transgene incorporation, and RNA expression. Sterile transformants were transferred to soil for propagation, selfed, and seeds collected for further examination.

Transgenic plants can also be generated via in planta methods. In planta methods which circumvent tissue culture requirements can be more cost effective and avoid potential mutations associated with plant tissue culture.

For the seed transformation protocol (Feldmann, K., (1992) In: Methods in Arabidopsis Research (eds. C. Koncz, N. H. Chua, J. Schell) pp 274–289), 2.4 grams of *Arabidopsis thaliana* (ecotype Wassilewskija) seeds were surface sterilized for 8 minutes in 5.25% (w/v) sodium hypochlorite containing 0.15% (v/v) Tween 20, then rinsed 6–7 times with sterile water. The seeds were apportioned among 40 125 ml flasks containing 40 ml cocultivation medium (CCM) (1×MS salts, 40 g/l sucrose, 10 mg/l thiamine, 0.5 mg/ml pyridoxine, 0.5 mg/ml nicotinic acid and 100 mg/l inositol, pH 6.0 with KOH). These seed-containing flasks were shaken (190 rpm, 22° C.) and the seeds allowed to imbibe with constant lighting (approximately 250 lux) for a period of 10–18 hours. The flasks were then shaken vigorously to loosen clumped seeds and seeds stuck to the walls of the flasks. A 5 ml aliquot of a fresh log phase culture (optical density of 0.75) of the appropriate Agrobacterium strain was added to each seed-containing flask. The Agrobacterium culture was grown without selective antibiotics at 28° C. in LB broth. The flasks were shaken for a 24 hour cocultivation period until the Agrobacterium reached stationary phase. Seeds were collected by filtration on filter paper, allowed to dry for 30 minutes in a fuime hood, and sown within one hour of drying the seeds. Seeds scraped off the filter paper were sown onto presoaked soil mixtures and covered with plastic wrap containing aeration slits. The seeds and resulting plants were maintained at 21° C. in growth chambers with a 16:8 light dark photoperiod (illumination at 100 ymoles per meter$^2$ per second) until maturity. The plants were watered daily with a nutrient solution such as Hoaglund's medium (per liter: Ca(NO$_3$)$_2$·H$_2$O, 1.1 g; MgSO$_4$·H$_2$O, 738 mg; KNO3, 505 mg; NH$_4$NO$_3$, 120 mg; KH$_2$PO$_4$, 8 mg; Chelated iron (supplied as Sequestrine 138-Fe, Ciba-Geigy Corp.), 15 mg; H$_3$BO$_3$, 2.1 mg; MnCl$_2$ ·H$_2$O, 1.4 mg; ZnSO$_4$·7H$_2$O, 165 µg; H$_3$MoO$_4$·H$_2$O, 68 µg; CuSO$_4$·5H$_2$O, 60 µg, adjusted to pH of 5.7–6.0 in soil with H$_2$SO$_4$). After approximately seven weeks, the plants were allowed to dry and the T2 seeds were bulk harvested. These seeds were then used for further screening and analysis.

Phenotypic observations of the primary generation of transgenic plants (*Lycopersicon esculentum, Brassica napus* and *Arabidopsis thaliana*) indicate that the transgenic plants produce seeds approximately twice the size of their wildtype counterparts or the control plants transformed with Agrobacterium harboring only the pEND4K plasmid. This phenotypic change may be a protein transport effect caused by the altered levels of Bce44B in the envelopes of plastids throughout all parts of the plant or at least in the seed tissues. Similar results have observed with transformed Brassica seeds.

Example 21
Monoclonal antibodies

Monoclonal antibodies (Mab's) specific for isolated or recombinant Bce44B proteins or polypeptides are useful, for example, for diagnostic purposes such as for determining Bce44B protein levels in the identification of cells which express Bce44B. To produce these antibodies, purified Bce44B protein or polypeptide is prepared. The protein or polypeptide is produced in bacterial cells as a fusion protein with glutathione-S-transferase using the vector pGEX2 (Pharmacia). This permits purification of the fusion protein by GSH affinity chromatography. In another approach, Bce44B protein is expressed as a fusion protein with the bacterial maltose binding domain. The fusion protein is thus recovered from bacterial extracts by passing the extract over an amylose resin column followed by elution of the fusion protein with maltose. For this fusion construct, the vector pMalC2, commercially available from New England Biolabs, is used. This vector has been used in the past, for example, to overexpress nuclear receptor proteins which were recovered in high yields for functional studies and the production of receptor specific antisera (Ohno et al. (1993) *Mechanisms of Development* 40:13–24). The preparation of a second fusion protein is also useful the preliminary screening of MAb's.

The generation of hybridomas expressing monoclonal antibodies recognizing Bce44B protein is carried out as follows: BALB/c mice are injected intraperitoneally with protein/adjuvant three times at one-month intervals, followed by a final injection into the tail vein shortly prior to cell fusion. Spleen cells are harvested and fused with NS-1 myeloma cells (American Type Culture Collection, Rockville, Md.) using polyethylene glycol 4000 according to standard protocols (Kennett (1979) Meth. Enzymol. 58:345–359; Mirski et al. (1989) *Cancer Res.* 49:5719–5724). The cell fusion process is carried out as described in more detail below.

The fused cells are plated into 96-well plates with peritoneal exudate cells and irradiated spleen cells from BALB/c mice as feeder layers and selection with hypoxanthine, aminopterin, and thymidine (HAT medium) is performed.

An ELISA assay is used as an initial screening procedure. 1–10 μg of purified Bce44B (cleaved from the fusion protein) in PBS is used to coat individual wells, and 50–100 μl per well of hybridoma supernatants is incubated. Horseradish peroxidase-conjugated anti-mouse antibodies are used for the colorimetric assay.

Positive hybridomas are cloned by limiting-dilution and grown to large-scale for freezing and antibody production. Various positive hybridomas are selected for usefulness in western blotting and immunohistochemistry, as well as for cross reactivity with transport proteins from different species.

Example 22
Fusion Protocol for Production of Mouse Hybridomas

Feeder cells (spleen and peritoneal exudate cells) are plated. 24 to 48 hours before fusion, mouse myeloma cells are taken off drug (8-azaguanine 20 μg/ml) and counted to ensure that there are at least $50 \times 10^6$ cells. 2 g of PEG 4000 are autoclaved in a glass tube for 15 minutes and maintained at 60° C. in a water bath for use or alternatively stored at room temperature and remelted in a 60° C. water bath when needed.

BALB/c mice are immunized as per desired schedule. The final injection is given intravenously in the tail vein. Fusion of immunized spleen cells is carried out 3 or 4 days after the intravenous injection. Spleen from each animal is collected separately; eye sera for ELISA if desired.

A single cell suspension is prepared using a Teflon pestle and decanting connective tissue. The suspension is washed 1× in serum-free medium. Each spleen has about $10 \times 10^6$ cells. The myeloma cells are collected, counted and washed in serum-free medium.

The cells are then fused. A small beaker of water, and serum-free medium (37° C.) are prepared and the PEG melted at 50–60° C. The immunized spleen cells and myeloma cells are mixed in a 50 ml TC tube (recommended ratios vary from 1:1 to 2:1) and the cells are washed once with serum-free medium. The supernatant is carefully discarded. 2.4 ml pre-warmed serum-free medium is added immediately with a pipette to the melted PEG and mixed, maintaining the temperature at 37° C. in a beaker of warm water. The PEG should be light pink. If it is yellow, another aliquot should be used. 0.5–1.0 ml of PEG is added dropwise to the cell pellet over 1 minute with gentle rotation of the tube or gentle stirring to ensure mixing. The tip of the addition pipette is placed directly over the cell pellet. The tube is swirled gently in a 37° C. water bath for 90 seconds with the blunt end of a 3 ml pipette tip and 10 ml warm serum-free medium added slowly over 6–10 minutes while rotating the tube gently to bring the volume up to 20–50 ml. The tube is maintained at 37° C. for at least 20 minutes to obtain cell fusion and then the cells are washed 2× with serum-free medium. The cells are centrifuged and gently resuspended in 100 ml of pre-warmed medium+10–20% Fetal Bovine Serum (FBS). 100 μl/well is aliquotted in 96-well plates. Assuming one spleen fused with $100 \times 10^6$ cells myeloma fusion partner, about 10 plates are needed. On the following day, 100 μl medium is removed and 100 μl 2× HAT added. Feed with 1× HAT medium for 1 to 3 weeks, then feed with HT medium (i.e., remove ½ HAT medium and replace with equal volume HT medium).

Example 23
Preparation of Peritoneal Exudates and Spleen Feeder Cells

A sacrificed mouse is sprayed with 70% alcohol, skin is nicked and torn apart, with care being taken not to cut the peritoneum. The peritoneum is lifted with forceps and a needle is introduced; 5 ml of serum-free medium is then slowly injected. The abdomen is massaged and the fluid is slowly sucked up, collected in a sterile tube and kept on ice. The volume is brought up to 5 ml. The spleen is obtained and placed in a sterile tube containing serum-free medium. The spleen is gently mashed with a sterile Teflon pestle. Clumps are allowed to settle and the cells are decanted into a clean tube, care being taken to avoid including connective tissue, in order to minimize fibroblast growth. The sample is irradiated at 4500 R. Cells are washed once with serum-free medium, placed into 96 well plates (one spleen/10 plates (approximately $2-5 \times 10^5$ cells/well) and peritoneal exudate cell suspension (PECS) ($<3 \times 1I0$ cells/well) in a total volume of 100 μl/well) and incubated at 37° C. until ready to be used. The cells can also be stored in sterile tube overnight at 4° C.

Example 24
Construction of *Pisum sativum* cDNA clones

Methods for constructing a *Pisum sativum* (cv. "Improved Paxton's") cDNA expression library and for imnmuno-screening the library were carried out as described in Ko, K. et al. (1992) *J. Biol. Chem.* 267:2986 and Ko, K. et al., (1994) *Plant Physiol.* 104:1087. The cDNA expression library was constructed in the phage vector λgt11 (Promega, Madison, Wis., USA) using polyadenylated RNA isolated from etiolated *Pisum sativum* (cv. "Improved Paxton's") seedlings. The synthesis of cDNA was facilitated using a kit purchased from Promega. The growth and propagation of the cDNA library were performed according to standard methods such as the ones described in *Molecular Cloning: A Laboratory Manual* (Sambrook et al. (1989) Cold Spring Harbor Laboratory, Cold Spring Harbor, N.Y.). The cDNA inserts were retrieved by an EcoRI-NotI digestion from the selected appropriate recombinant phage DNA and subcloned into pGEM11Z (Promega) for expression in JM109 (DE3) and for further analysis.

Example 25
Construction of *Ricinis communis* cDNA clones

Methods for constructing a *Ricinis communis* (castor bean) cDNA expression library and for immunoscreening the library were carried out as described in Ko, K. et al. (1992) *J. Biol. Chem.* 267:2986 and Ko, K. et al., (1994) *Plant Physiol.* 104:1087. The cDNA expression library was constructed in the phage vector λgt11 (Promega, Madison, Wis., USA) using polyadenylated RNA isolated from *Ricinis communis* endosperm. The synthesis of cDNA was facilitated using a kit purchased from Promega. The growth and propagation of the cDNA library were performed according to standard methods such as the ones described in *Molecular Cloning: A Laboratory Manual* (Sambrook et al. (1989) Cold Spring Harbor Laboratory, Cold Spring Harbor, N.Y.). The cDNA inserts were retrieved by an EcoRI-NotI digestion from the selected appropriate recombinant phage DNA and subcloned into pGEM11Z (Promega) for expression in JM109 (DE3) and for further analysis.

Example 26
Nucleotide sequence analysis

The nucleotide sequence of three cDNA inserts from *Pisum sativum* (cv. "Improved Paxton's") and three cDNA inserts from *Ricinis communis* are determined by standard dideoxynucleotide chain-tennination using double-stranded DNA templates (*Molecular Cloning: A Laboratory Manual*, Sambrook et al., (1989) Cold Spring Harbor Laboratory, Cold Spring Harbor, N.Y.).

Example 27
Transformation of yeast with Bce44B

Insert from the pGEM11 plasmid containing the Bce44B sequence was retrieved, gel-purified, and subcloned into the pYES2 yeast expression vector (InVitrogen, San Diego, Calif., USA) at the EcoRI and NotI sites, and transformed into *Saccharomyces cerevisiae* using the EasyComp™ kit (InVitrogen, San Diego, Calif., USA), following the manufacturer's instructions. The Bce44B-containing plasmid was digested with EcoRI, converted to a blunt and with Klenow fragment, and then digested with NotI. Yeast expression plasmid pYES2 was also digested with BstEII, converted to a blunt end with Kienow, and then digested with NotI, and the insert and the yeast plasmid were then ligated together, following the manufacturer's instructions. For transformation, 10 ml of YPAD (1% yeast extract, 2% peptone, 2% dextrose) was inoculated with strain "Invsc1" (InVitrogen, San Diego, Calif., USA), and incubated overnight at 30° C. with shaking. The culture was diluted to an $OD_{600}$ of 0.4 in 50 ml of YPAD and grown an additional 2–4 hours. The cells were then centrifuged at 2500 rpm, and the pellet resuspended in 40 ml of 1×TE (10×TE=100 mM Tris (pH 7.5), 10 mM EDTA). The cells were then centrifuged again at 2500 rpm, and the pellet resuspended in 2 ml of 1×LiAc/0.5×TE (10×LiAc=1 M lithium acetate, pH 7.5). The cells were incubated at room temperature for 10 minutes, then 1 µg of the plasmid DNA and 100 µg of denatured sheared salmon sperm DNA were mixed together with 100 µl of the re-suspended yeast cells. 700 µl of 1×LiAc/40% PEG-3350/1×TE (100 mM lithium acetate (pH 7.5), 40% PEG-3350, 10 mM Tris-HCl (pH 7.5)) were added, mixed well, and incubated at 30° C. for 30 minutes. After incubation, 88 µl of DMSO were added, mixed, and a 7-minute heat shock of 42° C. applied. The mixture was then centrifuged in a microcentrifuge for 10 seconds, and the supernatant removed. The pellet was resuspended in 1 ml of 1×TE, the mixture re-centrifuged, and the pellet then resuspended in 50–100 µl TE and plated on YC selective media (uracil-minus) (0.12% yeast nitrogen base (without either amino acids or ammonium sulfate), 0.5% ammonium sulfate, 1% succinic acid, 0.6% NaOH, 2% glucose, 0.01% of the following amino acids: adenine, arginine, cysteine, leucine, lysine, threonine, tryptophan; and 0.005% of the following amino acids: aspartic acid, histidine, isoleucine, methionine, phenylalanine, proline, serine, tyrosine, valine).

The resulting clones were screened for expression by Western blot. A single transformed colony was inoculated into 5 ml of YPAD, which was then shaken overnight at 30° C. The cells were then centrifuged for 5 minutes at 2500 rpm, the medium decanted, and the tube containing the pellet placed at −80° C. for 10 minutes. The pellet was then thawed in 100 µl of prewarned (60° C.) cracking buffer (8M urea, 5% SDS, 40 mM Tris-HCl (pH 6.8), 0.1 mM EDTA, 1% β-mercaptoethanol, 0.4 mg/ml bromophenol blue) and resuspended by pipetting. The cell suspension was then transferred to a 1.5 ml microcentrifuge tube containing 100 µl of glass beads, and incubated at 70° C. for 10 minutes. The suspension was then mixed by vortexing for 1 minute, and centrifuged at 1400 rpm for 5 minutes at room temperature. The supernatant was then transferred to a new tube. SDS-PAGE buffer was then added to the supernatant, and the sample boiled for 5 minutes. 30–50 µl were used for Western blot analysis, which indicated expression of the Bce44B protein in the yeast cells.

All patents, patent applications, and references cited above are hereby incorporated by reference in their entirety. While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for enhancing transport of a substance across or into a cellular membrane, the method comprising:
   a) incorporating into a cell or organism, at least one isolated or recombinant nucleic acid encoding a plastid membrane transport polypeptide which:
      i) is hybridizable under high stringency conditions to a nucleic acid encoding a polypeptide comprising at least 17 consecutive amino acid residues between residues 43 and 323 of SEQ ID NO:2, wherein said high stringency conditions comprise prehybridization in 50% formamide, 5×SSC, 25 mM potassium phosphate buffer (pH 7.4), 5×Denhardt's, and 50 µg/ml denatured salmon sperm DNA for 4–12 hours at 37° C., followed by hybridization for 12–24 hours at 37° C. and washing in 2×SSC containing 0.1% SDS, at 55° C.; or
      ii) encodes a polypeptide comprising 17 consecutive amino acid residues between residues 43 and 323 of SEQ ID NO:2; or
      iii) encodes a plastid membrane transport protein having an apparent molecular mass of 42 to 46 kDa on an SDS polyacrylamide gel, which binds to antibodies that bind to a protein having the amino acid sequence of SEQ ID NO:2; or
      iv) has two or more of the above characterstics; and
   b) maintaining the cell or organism so that the encoded polypeptide is expressed, wherein transport of said substance is enhanced.

2. The method according to claim 1, wherein the substance is a peptide, polypeptide, protein, or molecule with a peptide bond.

3. The method according to claim 1 wherein the cell or organism is prokaryotic.

4. The method of claim 1, wherein the cell or organism is *E. coli*.

5. The method according to claim 1 wherein the cell or organism is eukaryotic.

6. The method according to claim 1 wherein the membrane is a plastid or mitochondrial membrane.

7. The method according to claim 1, wherein the cell is in a tissue culture.

8. The method of claim 1, further comprising incorporating into the cell or organism, a nucleotide sequence encoding a substance to be transported.

9. A method for enhancing transport of a substance across or into a Brassica, Pisum or Lycopersicon cellular membrane, the method comprising:
   a) incorporating into a cell, protoplast, plant, plant part, or tissue culture of Brassica, Pisum or Lycopersicon, at least one isolated or recombinant nucleic acid encoding a plastid membrane transport polypeptide which:
      i) is hybridizable under high stringency conditions to a nucleic acid encoding a polypeptide comprising at least 17 consecutive amino acid residues between residues 43 and 323 of SEQ ID NO:2 wherein said high stringency conditions comprise prehybridization in 50% formamide, 5×SSC, 25 mM potassium phosphate buffer (pH 7.4), 5×Denhardt's, and 50 µg/ml denatured salmon sperm DNA for 4–12 hours at 37° C., followed by hybridization for 12–24 hours at 37° C. and washing in 2×SSC containing 0.1% SDS, at 55° C.; or
      ii) encodes a polypeptide comprising 17 consecutive amino acid residues between residues 43 and 323 of SEQ ID NO:2; or
      iii) encodes a plastid membrane transport protein having an apparent molecular mass of 42 to 46 kDa on an SDS polyacrylamide gel, which binds to antibodies that bind to a protein having the amino acid sequence of SEQ ID NO:2; or
      iv) has two or more of the above characteristics; and
   b) maintaining the cell, protoplast, plant, plant part, or tissue culture of Brassica, Pisum or Lycopersicon so that the encoded polypeptide is expressed, wherein transport of said substance is enhanced, relative to a corresponding cell, protoplast, plant, plant part, or tissue culture of Brassica, Pisum or Lycopersicon into which no such isolated or recombinant nucleic acid has been incorporated.

10. The method of claim 9, further comprising incorporating into the cell, protoplast, plant, plant part, or tissue culture, a nucleotide sequence encoding a substance to be transported.

* * * * *

SEQUENCE LISTING

<160> NUMBER OF SEQ ID NOS: 5

<210> SEQ ID NO 1
<211> LENGTH: 1193
<212> TYPE: DNA

-continued

```
<213> ORGANISM: Brassica napus
<220> FEATURE:
<221> NAME/KEY: CDS
<222> LOCATION: (123)...(1091)

<400> SEQUENCE: 1
cgttgctgtc ggccaccacc accatcttcg tcaaccatag gatcacactt t tctggattg      60 gtgttggggt tgggctatca gctttgttct catgggtaac ctcaaacgca a agaaatatg    120 ca atg caa aca gct atg aag aca atg atg aa c cag atg aat acg caa        167
   Met Gln Thr Ala Met Lys Thr Met Met    Asn Gln Met Asn Thr Gln
   1               5                 10                    15 aac agc cag ttt aat aat cct gga ttc cca a ca ggg gca gga gca gga        215
Asn Ser Gln Phe Asn Asn Pro Gly Phe Pro T hr Gly Ala Gly Ala Gly
                20                  25                     30 gca gga tca cct ttt ccg ttt cca ttt cct c ct caa aca agt cct act        263
Ala Gly Ser Pro Phe Pro Phe Pro Phe Pro P ro Gln Thr Ser Pro Thr
            35                  40                     45 acc tct ccg ttc cag cct caa tcc cag tct t ca ggt gct act gtt gat        311
Thr Ser Pro Phe Gln Pro Gln Ser Gln Ser S er Gly Ala Thr Val Asp
        50                  55                     60 ctg aca gct aca aaa gta gat agg cct cct g tg tct aag cca caa cct        359
Leu Thr Ala Thr Lys Val Asp Arg Pro Pro V al Ser Lys Pro Gln Pro
    65                  70                     75 aca cct ata cct cct aca aag agc ata gaa g tg tat aaa cca agt gtt        407
Thr Pro Ile Pro Pro Thr Lys Ser Ile Glu V al Tyr Lys Pro Ser Val
80                  85                      90                 95 gtc gta gag gaa aac aaa gcg atg aaa gaa g aa aag aac tac gct ttt        455
Val Val Glu Glu Asn Lys Ala Met Lys Glu G lu Lys Asn Tyr Ala Phe
                100                 105                    110 gaa gac gtt tcc cct gag gaa acc aca aag g aa agt cca ttt agc aac        503
Glu Asp Val Ser Pro Glu Glu Thr Thr Lys G lu Ser Pro Phe Ser Asn
            115                 120                    125 tat gaa gaa gtc tct gaa act agt gcc ccc a aa gaa act cgc tta ttt        551
Tyr Glu Glu Val Ser Glu Thr Ser Ala Pro L ys Glu Thr Arg Leu Phe
        130                 135                    140 gac gat gtt ctg caa aat gga gct gct ccg g cc aat ggt gcc act gct        599
Asp Asp Val Leu Gln Asn Gly Ala Ala Pro A la Asn Gly Ala Thr Ala
    145                 150                    155 tca gat gtt ttt caa tct ttg ggc gct ggg a aa gga tgg gct ggt ggg        647
Ser Asp Val Phe Gln Ser Leu Gly Ala Gly L ys Gly Trp Ala Gly Gly
160                 165                     170                175 tca gta gaa gtt tta gag aaa atg ata gaa t at ccc aca ttt cag aag        695
Ser Val Glu Val Leu Glu Lys Met Ile Glu T yr Pro Thr Phe Gln Lys
                180                 185                    190 atg ctt tac cca cat ttg cct gag gag atg a gg aac cca gaa agt ttc        743
Met Leu Tyr Pro His Leu Pro Glu Glu Met A rg Asn Pro Glu Ser Phe
            195                 200                    205 aaa tgg gtg cgt aag aat cct caa tac cgt c aa cag cta cag gac atg        791
Lys Trp Val Arg Lys Asn Pro Gln Tyr Arg G ln Gln Leu Gln Asp Met
        210                 215                    220 ttg aat aat atg agt gag agt ggt gaa tgg g ac aag aga atg acg gag        839
Leu Asn Asn Met Ser Glu Ser Gly Glu Trp A sp Lys Arg Met Thr Glu
    225                 230                    235 acc tta aag aat ttt gac ccg aat agc ccc g aa gtt aag caa gga ttc        887
Thr Leu Lys Asn Phe Asp Pro Asn Ser Pro G lu Val Lys Gln Gly Phe
240                 245                     250                255 gat caa tta gga ctg act cca gaa gaa gtc a tc tct aag ata atg gag        935
Asp Gln Leu Gly Leu Thr Pro Glu Glu Val I le Ser Lys Ile Met Glu
                260                 265                    270
```

```
aac cct gat gtt tca atg gca ttc cag aat c ct aga gtc gaa gca gcg       983
Asn Pro Asp Val Ser Met Ala Phe Gln Asn P ro Arg Val Glu Ala Ala
        275                 280                  285 tta atg gac tgc tca gag aac ccg atg aac a tc atg aag tac caa aat      1031
Leu Met Asp Cys Ser Glu Asn Pro Met Asn I le Met Lys Tyr Gln Asn
        290                 295                 300 gac aaa gag gta atg gat gtg ttc aac aag a ta tcg cag ctc ttc cca      1079
Asp Lys Glu Val Met Asp Val Phe Asn Lys I le Ser Gln Leu Phe Pro
    305                 310                 315 gga ttg acg ggt tgaaaggct cgctgatcac gtcttttggt t taatgactt           1131
Gly Leu Thr Gly
320 ttatcttatt ggatcagagg ttcatgtctt tctttagctt tgtaccactg a gaaaaaaaa   1191 aa                                                                    1193

<210> SEQ ID NO 2
<211> LENGTH: 323
<212> TYPE: PRT
<213> ORGANISM: Brassica napus

<400> SEQUENCE: 2

Met Gln Thr Ala Met Lys Thr Met Met Asn G ln Met Asn Thr Gln Asn
 1               5                  10                  15

Ser Gln Phe Asn Asn Pro Gly Phe Pro Thr G ly Ala Gly Ala Gly Ala
            20                  25                  30

Gly Ser Pro Phe Pro Phe Pro Phe Pro Pro G ln Thr Ser Pro Thr Thr
        35                  40                  45

Ser Pro Phe Gln Pro Gln Ser Gln Ser Ser G ly Ala Thr Val Asp Leu
    50                  55                  60

Thr Ala Thr Lys Val Asp Arg Pro Pro Val S er Lys Pro Gln Pro Thr
65                  70                  75                  80

Pro Ile Pro Pro Thr Lys Ser Ile Glu Val T yr Lys Pro Ser Val Val
                85                  90                  95

Val Glu Glu Asn Lys Ala Met Lys Glu Glu L ys Asn Tyr Ala Phe Glu
            100                 105                 110

Asp Val Ser Pro Glu Glu Thr Thr Lys Glu S er Pro Phe Ser Asn Tyr
        115                 120                 125

Glu Glu Val Ser Glu Thr Ser Ala Pro Lys G lu Thr Arg Leu Phe Asp
    130                 135                 140

Asp Val Leu Gln Asn Gly Ala Ala Pro Ala A sn Gly Ala Thr Ala Ser
145                 150                 155                 160

Asp Val Phe Gln Ser Leu Gly Ala Gly Lys G ly Trp Ala Gly Gly Ser
                165                 170                 175

Val Glu Val Leu Glu Lys Met Ile Glu Tyr P ro Thr Phe Gln Lys Met
            180                 185                 190

Leu Tyr Pro His Leu Pro Glu Glu Met Arg A sn Pro Glu Ser Phe Lys
        195                 200                 205

Trp Val Arg Lys Asn Pro Gln Tyr Arg Gln G ln Leu Gln Asp Met Leu
    210                 215                 220

Asn Asn Met Ser Glu Ser Gly Glu Trp Asp L ys Arg Met Thr Glu Thr
225                 230                 235                 240

Leu Lys Asn Phe Asp Pro Asn Ser Pro Glu V al Lys Gln Gly Phe Asp
                245                 250                 255

Gln Leu Gly Leu Thr Pro Glu Glu Val Ile S er Lys Ile Met Glu Asn
            260                 265                 270
```

```
Pro Asp Val Ser Met Ala Phe Gln Asn Pro A rg Val Glu Ala Ala Leu
        275                 280                 285

Met Asp Cys Ser Glu Asn Pro Met Asn Ile M et Lys Tyr Gln Asn Asp
        290                 295                 300

Lys Glu Val Met Asp Val Phe Asn Lys Ile S er Gln Leu Phe Pro Gly
305                 310                 315                 320

Leu Thr Gly

<210> SEQ ID NO 3
<211> LENGTH: 878
<212> TYPE: DNA
<213> ORGANISM: Lycopersicon esculentum
<220> FEATURE:
<221> NAME/KEY: CDS
<222> LOCATION: (3)...(698)

<400> SEQUENCE: 3 ga ttt ggt tca aat aca tct gac agt acc tc a tca acg gga aaa tct         47
    Phe Gly Ser Asn Thr Ser Asp Ser Thr  Ser Ser Thr Gly Lys Ser
     1               5                    10                  15 aat cct cta ttg tcg gtg gat gct ctg gag a aa atg atg gaa gat cca        95
Asn Pro Leu Leu Ser Val Asp Ala Leu Glu L ys Met Met Glu Asp Pro
                 20                  25                  30 aca gtg cag aag atg gtt tac ccc tat cta c cc gag gag atg agg aac       143
Thr Val Gln Lys Met Val Tyr Pro Tyr Leu P ro Glu Glu Met Arg Asn
             35                  40                  45 cct aca aca tta aaa tgg atg cta caa aat c ca caa tac cgt caa cag       191
Pro Thr Thr Leu Lys Trp Met Leu Gln Asn P ro Gln Tyr Arg Gln Gln
         50                  55                  60 ttg cag gac atg atg aat aac atg ggt gga a ac cca gaa tgg gac aac       239
Leu Gln Asp Met Met Asn Asn Met Gly Gly A sn Pro Glu Trp Asp Asn
 65                  70                  75 cgc atg atg gat tcc ttg aag aat ttt gat c tc agc agc cct gaa atc       287
Arg Met Met Asp Ser Leu Lys Asn Phe Asp L eu Ser Ser Pro Glu Ile
 80                  85                  90                  95 aag caa caa ttt gat cag ata gga ctt act c cc gag gaa gtc att tcg       335
Lys Gln Gln Phe Asp Gln Ile Gly Leu Thr P ro Glu Glu Val Ile Ser
                100                 105                 110 aag att atg gag aat cct gat gtt gcc atg g ct ttc caa aat cca aga       383
Lys Ile Met Glu Asn Pro Asp Val Ala Met A la Phe Gln Asn Pro Arg
            115                 120                 125 gtt caa gca gcc atc atg gat tgt gct cag a at cca ctg agt att gca       431
Val Gln Ala Ala Ile Met Asp Cys Ala Gln A sn Pro Leu Ser Ile Ala
        130                 135                 140 aaa tac caa aat gac aag gag gtg atg gac g tc ttc aac aaa ata tca       479
Lys Tyr Gln Asn Asp Lys Glu Val Met Asp V al Phe Asn Lys Ile Ser
145                 150                 155 gaa cta ttc cct ggg gtg gca gtg gcg cct t gc tta tct ccg tcc tgc       527
Glu Leu Phe Pro Gly Val Ala Val Ala Pro C ys Leu Ser Pro Ser Cys
160                 165                 170                 175 cta agc agc tat tat gtt aca acg att gca t tt ttg ttc tgt ttg agt       575
Leu Ser Ser Tyr Tyr Val Thr Thr Ile Ala P he Leu Phe Cys Leu Ser
                180                 185                 190 gaa gta tca gtc aga agt gtg ggc tct gag a tg gag ttt tcg ccc tct       623
Glu Val Ser Val Arg Ser Val Gly Ser Glu M et Glu Phe Ser Pro Ser
            195                 200                 205 gtt gca act cgg atg cac atg aaa acg tcg c tt cct tta tat aaa ttc       671
Val Ala Thr Arg Met His Met Lys Thr Ser L eu Pro Leu Tyr Lys Phe
        210                 215                 220 att gcc ctt ctc aaa ttt tgt gga ttg taacatac tt gccttggctt            718
```

```
Ile Ala Leu Leu Lys Phe Cys Gly Leu
    225                 230 accagtagtg tttagaagcc aatttcagtg tgatatttgc cagtttcttt a tggttttag      778 agttacttaa gcttattcaa ctgttatgat ttgatgaaac ggaggaataa a aattttatt     838 caataattac ttcaattaaa aaaaaaaaaa aaaaaaaaaa                              878

<210> SEQ ID NO 4
<211> LENGTH: 232
<212> TYPE: PRT
<213> ORGANISM: Lycopersicon esculentum

<400> SEQUENCE: 4

Phe Gly Ser Asn Thr Ser Asp Ser Thr Ser S er Thr Gly Lys Ser Asn
  1               5                  10                  15

Pro Leu Leu Ser Val Asp Ala Leu Glu Lys M et Met Glu Asp Pro Thr
             20                  25                  30

Val Gln Lys Met Val Tyr Pro Tyr Leu Pro G lu Glu Met Arg Asn Pro
         35                  40                  45

Thr Thr Leu Lys Trp Met Leu Gln Asn Pro G ln Tyr Arg Gln Gln Leu
     50                  55                  60

Gln Asp Met Met Asn Asn Met Gly Gly Asn P ro Glu Trp Asp Asn Arg
 65                  70                  75                  80

Met Met Asp Ser Leu Lys Asn Phe Asp Leu S er Ser Pro Glu Ile Lys
                 85                  90                  95

Gln Gln Phe Asp Gln Ile Gly Leu Thr Pro G lu Glu Val Ile Ser Lys
            100                 105                 110

Ile Met Glu Asn Pro Asp Val Ala Met Ala P he Gln Asn Pro Arg Val
        115                 120                 125

Gln Ala Ala Ile Met Asp Cys Ala Gln Asn P ro Leu Ser Ile Ala Lys
    130                 135                 140

Tyr Gln Asn Asp Lys Glu Val Met Asp Val P he Asn Lys Ile Ser Glu
145                 150                 155                 160

Leu Phe Pro Gly Val Ala Val Ala Pro Cys L eu Ser Pro Ser Cys Leu
                165                 170                 175

Ser Ser Tyr Tyr Val Thr Thr Ile Ala Phe L eu Phe Cys Leu Ser Glu
            180                 185                 190

Val Ser Val Arg Ser Val Gly Ser Glu Met G lu Phe Ser Pro Ser Val
        195                 200                 205

Ala Thr Arg Met His Met Lys Thr Ser Leu P ro Leu Tyr Lys Phe Ile
    210                 215                 220

Ala Leu Leu Lys Phe Cys Gly Leu
225                 230

<210> SEQ ID NO 5
<211> LENGTH: 169
<212> TYPE: PRT
<213> ORGANISM: Brassica napus

<400> SEQUENCE: 5

Pro Leu Leu Ser Ala Tyr Lys Val Phe Gln S er Leu Gly Ala Gly Lys
  1               5                  10                  15

Gly Gly Ala Gly Leu Ser Val Glu Ala Leu G lu Lys Met Met Glu Asp
             20                  25                  30

Pro Thr Val Gln Lys Met Val Tyr Pro His L eu Pro Glu Glu Met Arg
         35                  40                  45
```

```
Asn Pro Glu Thr Leu Lys Trp Met Leu Gln A sn Pro Gln Tyr Arg Gln
        50              55              60

Gln Leu Gln Asp Met Leu Asn Asn Met Ser G ly Ser Gly Glu Trp Asp
65              70              75              80

Lys Arg Met Thr Glu Thr Leu Lys Asn Phe A sp Leu Asn Ser Pro Glu
                85              90              95

Val Lys Gln His Phe Asp Gln Ile Gly Leu T hr Pro Glu Glu Val Ile
            100             105             110

Ser Lys Ile Met Gln Asn Pro Asp Val Ala M et Ala Phe Gln Asn Pro
            115             120             125

Arg Val Gln Ala Ala Leu Met Glu Cys Ser G lu Asn Pro Met Asn Ile
        130             135             140

Met Lys Tyr Gln Asn Asp Lys Glu Val Met A sp Val Phe Asn Lys Ile
145             150             155             160

Ser Gln Leu Phe Pro Gly Met Thr Gly
                165
```